(12) United States Patent
Kawaguchi et al.

(10) Patent No.: US 10,045,793 B2
(45) Date of Patent: Aug. 14, 2018

(54) SURGICAL TREATMENT INSTRUMENT

(71) Applicant: OLYMPUS CORPORATION, Hachioji-shi, Tokyo (JP)

(72) Inventors: Yuki Kawaguchi, Koshu (JP); Yasuo Funakoshi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/469,246

(22) Filed: Mar. 24, 2017

(65) Prior Publication Data

US 2017/0196584 A1    Jul. 13, 2017

Related U.S. Application Data

(63) Continuation of application No. PCT/JP2015/081967, filed on Nov. 13, 2015.

(30) Foreign Application Priority Data

Nov. 21, 2014   (JP) .................. 2014-236977

(51) Int. Cl.
*A61B 17/32* (2006.01)
*A61N 7/02* (2006.01)
*A61B 17/00* (2006.01)

(52) U.S. Cl.
CPC ........... *A61B 17/320068* (2013.01); *A61B 17/320092* (2013.01); *A61N 7/02* (2013.01);
(Continued)

(58) Field of Classification Search
CPC .. A61B 17/320068; A61B 2017/00862; A61B 2017/320084; A61B 2017/3441;
(Continued)

(56) References Cited

U.S. PATENT DOCUMENTS

| 5,935,144 A | * | 8/1999 | Estabrook | ...... | A61B 17/320068 |
| | | | | | 604/22 |
| 5,944,737 A | | 8/1999 | Tsonton et al. | | |

(Continued)

FOREIGN PATENT DOCUMENTS

| JP | 2001-346806 A | 12/2001 |
| WO | 2014/045687 A1 | 3/2014 |

OTHER PUBLICATIONS

Jan. 26, 2016 Search Report issued in International Patent Application No. PCT/JP2015/081967.
(Continued)

*Primary Examiner* — Joseph Stoklosa
*Assistant Examiner* — Sean W Collins
(74) *Attorney, Agent, or Firm* — Oliff PLC

(57) ABSTRACT

In a surgical treatment instrument, a probe extending in a longitudinal axial direction is inserted through a sheath, and each of sheath components, in the sheath, is divided from a neighboring sheath component at a dividing plane along the longitudinal axial direction. A flow of liquid to a proximal side in an inside of the sheath is prevented by a first seal portion. In a divided part between each of the sheath components and the neighboring sheath component, liquid-tight is kept by the second seal portion, and thereby a flow of the liquid to the proximal side is prevented.

15 Claims, 16 Drawing Sheets

(52) U.S. Cl.
CPC .............. *A61B 2017/00862* (2013.01); *A61B 2017/320084* (2013.01)

(58) Field of Classification Search
CPC .......... A61B 17/22004; A61B 17/2202; A61B 1/00137; A61N 7/02
USPC ........................................................ 600/136
See application file for complete search history.

(56) References Cited

U.S. PATENT DOCUMENTS

| | | |
|---|---|---|
| 2002/0143355 A1 | 10/2002 | Messerly |
| 2011/0196398 A1 | 8/2011 | Robertson et al. |
| 2013/0345701 A1* | 12/2013 | Allen, IV ............. A61B 18/082 606/41 |
| 2014/0324084 A1 | 10/2014 | Sanai et al. |

OTHER PUBLICATIONS

Extended European Search Report issued in European Patent Application No. 15862063.3.

* cited by examiner

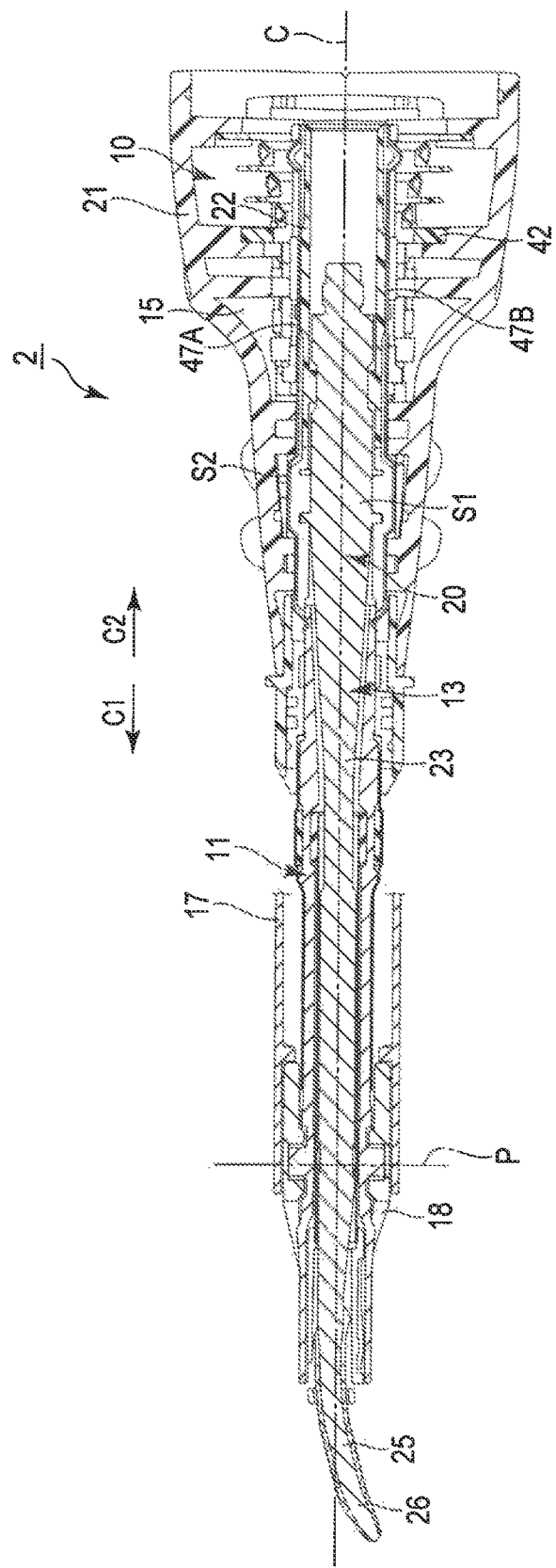
F I G. 3

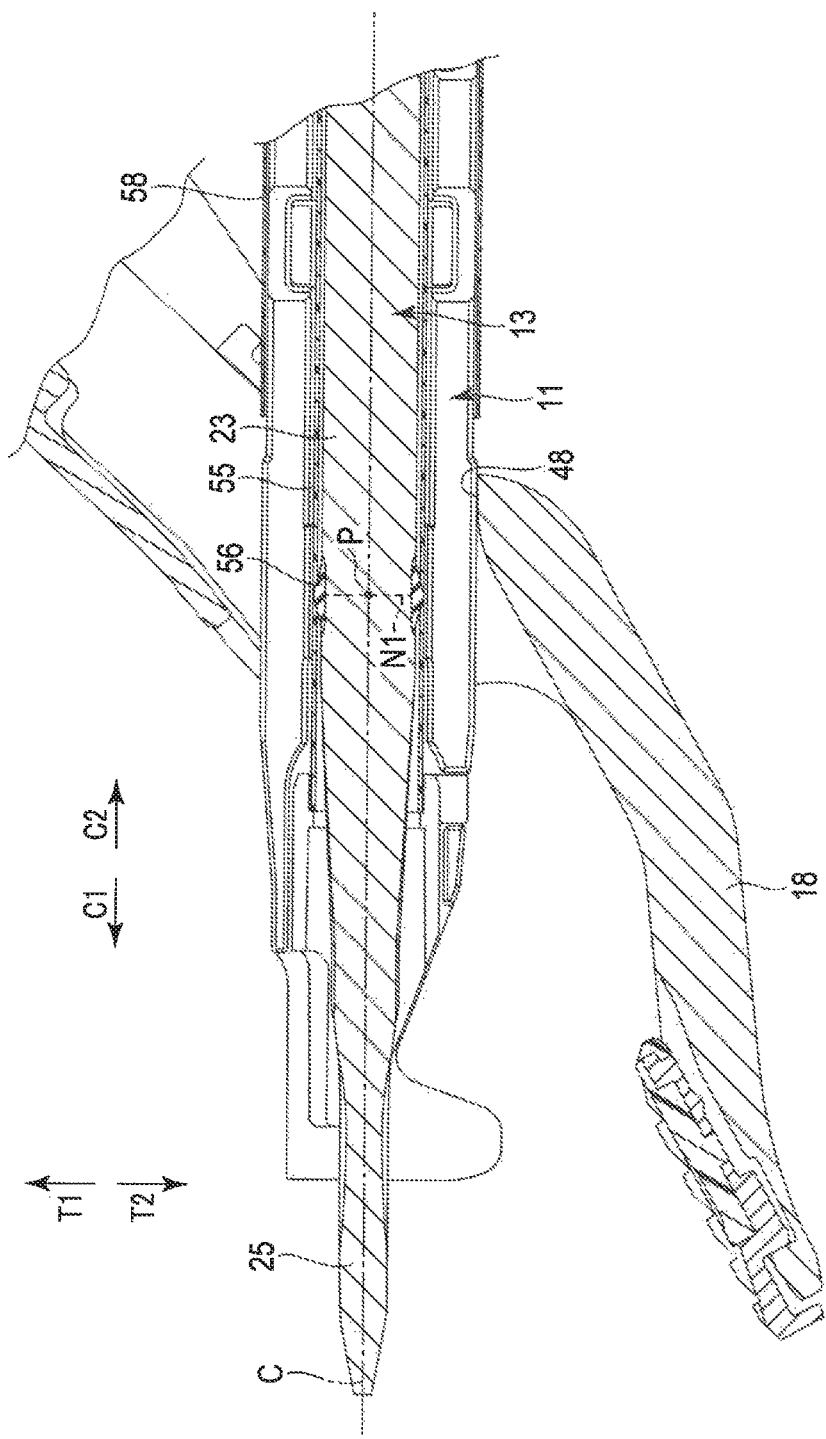
F I G. 5

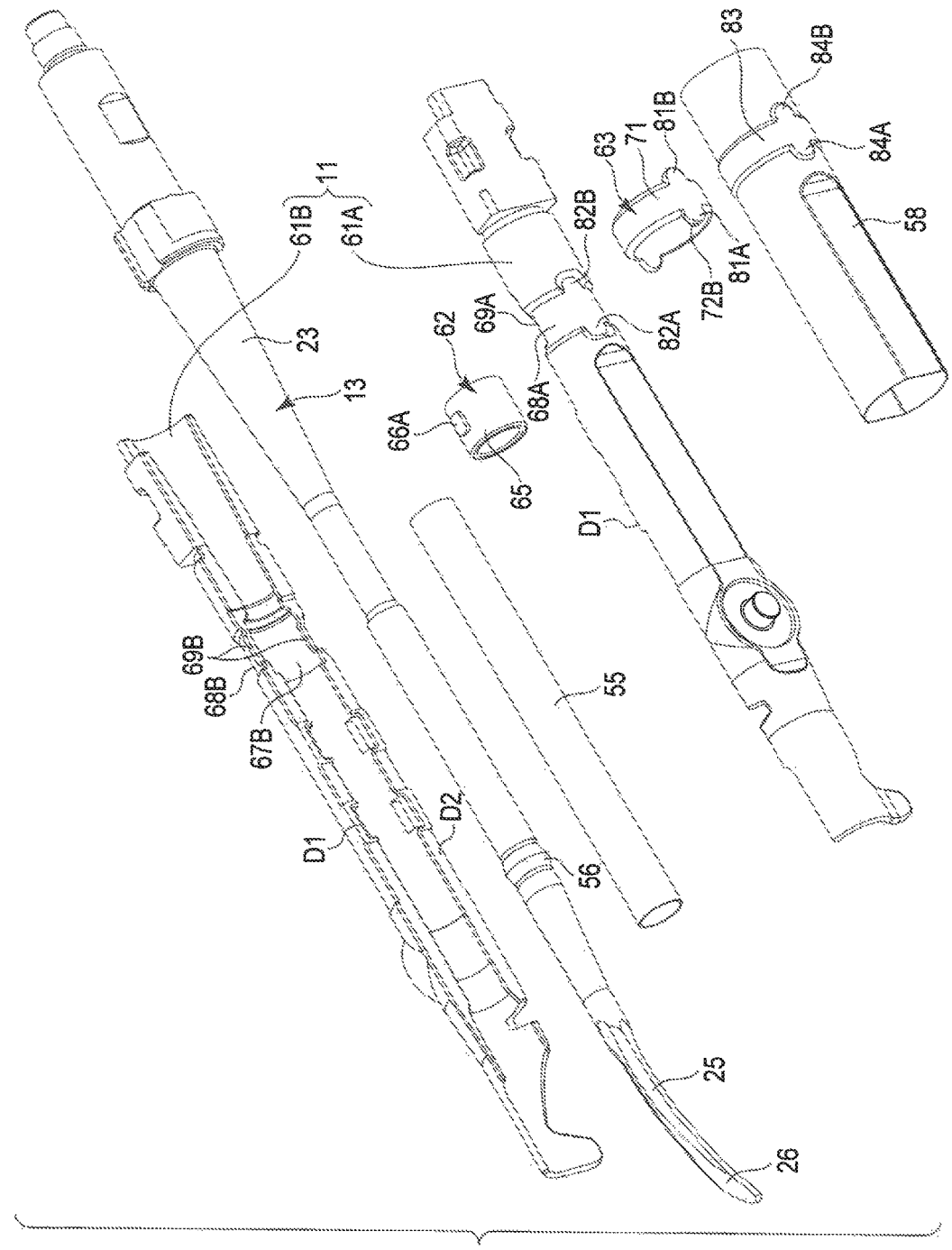
F I G. 6

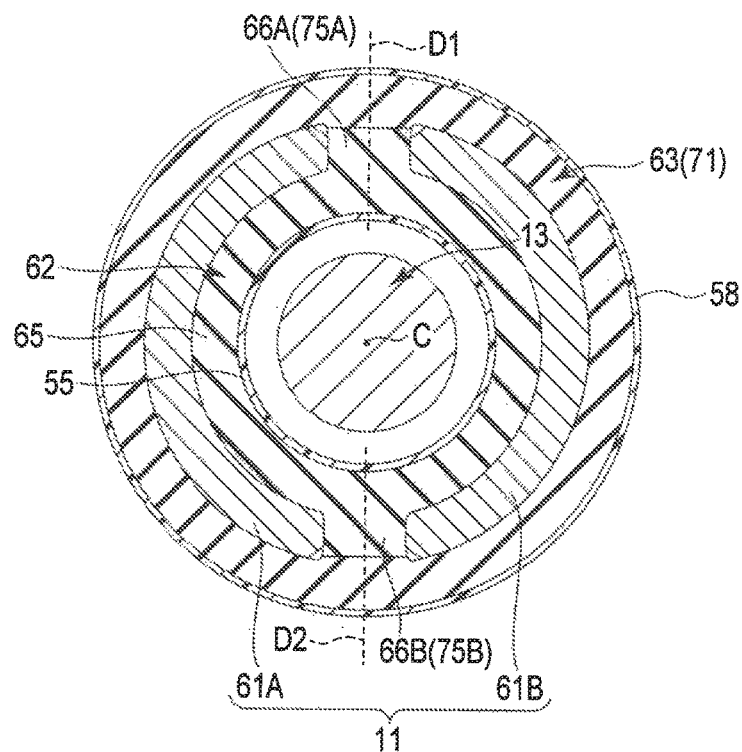
F I G. 9
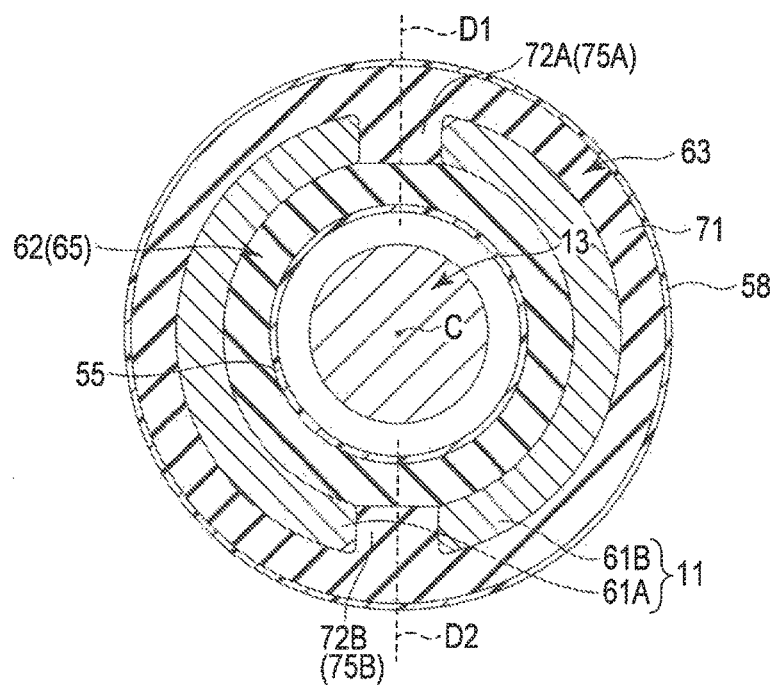
F I G. 10

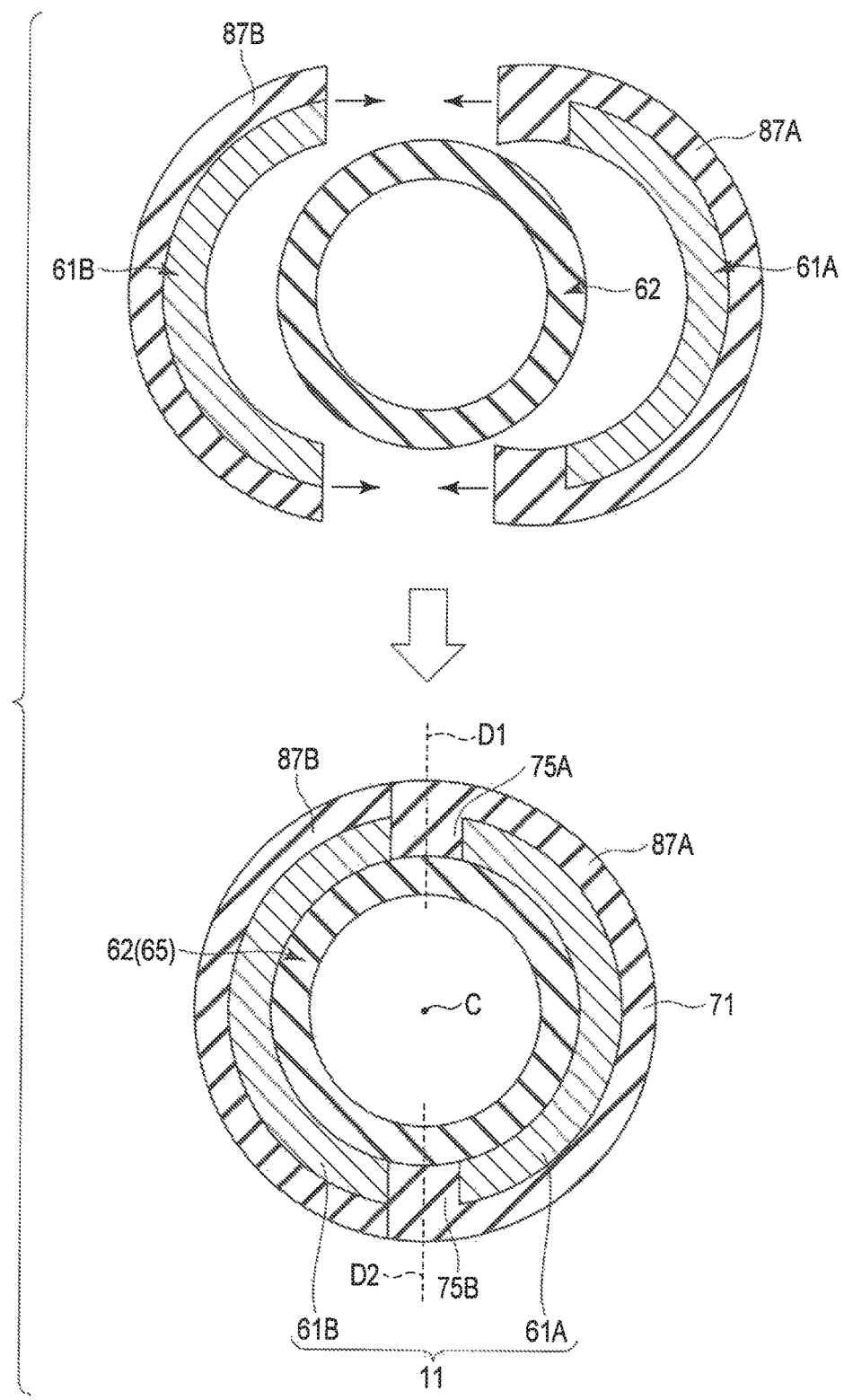
F I G. 13

SURGICAL TREATMENT INSTRUMENT

CROSS-REFERENCE TO RELATED APPLICATIONS

This is a Continuation application of PCT Application No. PCT/JP2015/081967, filed Nov. 13, 2015 and based upon and claiming the benefit of priority from prior Japanese Patent Application No. 2014-236977, filed Nov. 21, 2014, the entire contents of which are incorporated herein by reference.

BACKGROUND OF THE INVENTION

1. Field of the Invention

The present invention relates to a surgical treatment instrument including a probe and a sheath through which the probe is inserted.

2. Description of the Related Art

U.S. Patent Application Publication No. 2002/0143355 discloses a surgical treatment instrument including a probe which extends in a longitudinal axial direction, and a sheath through which the probe is inserted. In this surgical treatment instrument, a probe treatment portion is provided in a distal portion of the probe, and the probe treatment portion projects from a distal end of the sheath toward the distal side. In addition, the surgical treatment instrument includes a held unit which is composed of a held main body and a stationary handle. The probe and sheath are inserted in the inside of the held unit from the distal side, and are coupled to the held unit. In addition, a movable handle is openably and closably attached to the held unit, and a jaw is rotatably attached to a distal portion of the sheath. By opening or closing the movable handle relative to the held unit, the jaw rotates and the jaw opens or closes relative to the probe treatment portion. In the surgical treatment instrument, the jaw is closed relative to the probe treatment portion, and a treated target, such as a biological tissue, is grasped between the jaw and the probe treatment portion. The grasped treated target is treated by using energy such as ultrasonic vibration.

BRIEF SUMMARY OF THE INVENTION

According to one aspect of the invention, a surgical treatment instrument including: a probe having a proximal end and a distal end, and extending in a longitudinal axial direction; a sheath including a plurality of sheath components which are divided at a dividing plane along the longitudinal axial direction, and extending in the longitudinal axial direction, the sheath being configured to have such a cylindrical shape that the probe is insertable therethrough by the plurality of sheath components being abutted on each other at the dividing plane; a first seal portion provided between the sheath and the probe in a radial direction, and configured to prevent a flow of liquid to a proximal side in an inside of the sheath; and a second seal portion configured to keep liquid-tight a divided part between each of the sheath components and the neighboring sheath component, and configured to prevent a flow of the liquid to the proximal side at the divided part of each of the sheath components from the neighboring sheath component.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a cross-sectional view which schematically illustrates, in cross section perpendicular to a first crossing direction and a second crossing direction, the surgical treatment instrument according to the first embodiment, FIG. 5 is a cross-sectional view illustrating, in enlarged scale, a region V in FIG. 2, FIG. 6 is an exploded perspective view which schematically illustrates respective parts of a configuration located on a distal side with respect to a held unit in the surgical treatment instrument according to the first embodiment, with a movable handle and jaw being omitted, FIG. 9 is a cross-sectional view which schematically illustrates a cross section which is perpendicular to a longitudinal axis and passes through an inner seal portion, a relay seal portion and an outer seal portion according to a first modification, FIG. 10 is a cross-sectional view which schematically illustrates a cross section which is perpendicular to a longitudinal axis and passes through an inner seal portion, a relay seal portion and an outer seal portion according to a second modification, FIG. 13 is a cross-sectional view which schematically illustrates, in cross section perpendicular to a longitudinal axis, an inner seal portion, a relay seal portion, an outer seal portion and a sheath according to a fifth modification.

DETAILED DESCRIPTION OF THE INVENTION

First Embodiment

A first embodiment of the present invention will be described with reference to FIG. 1 to FIG. 8.

Figure 1:
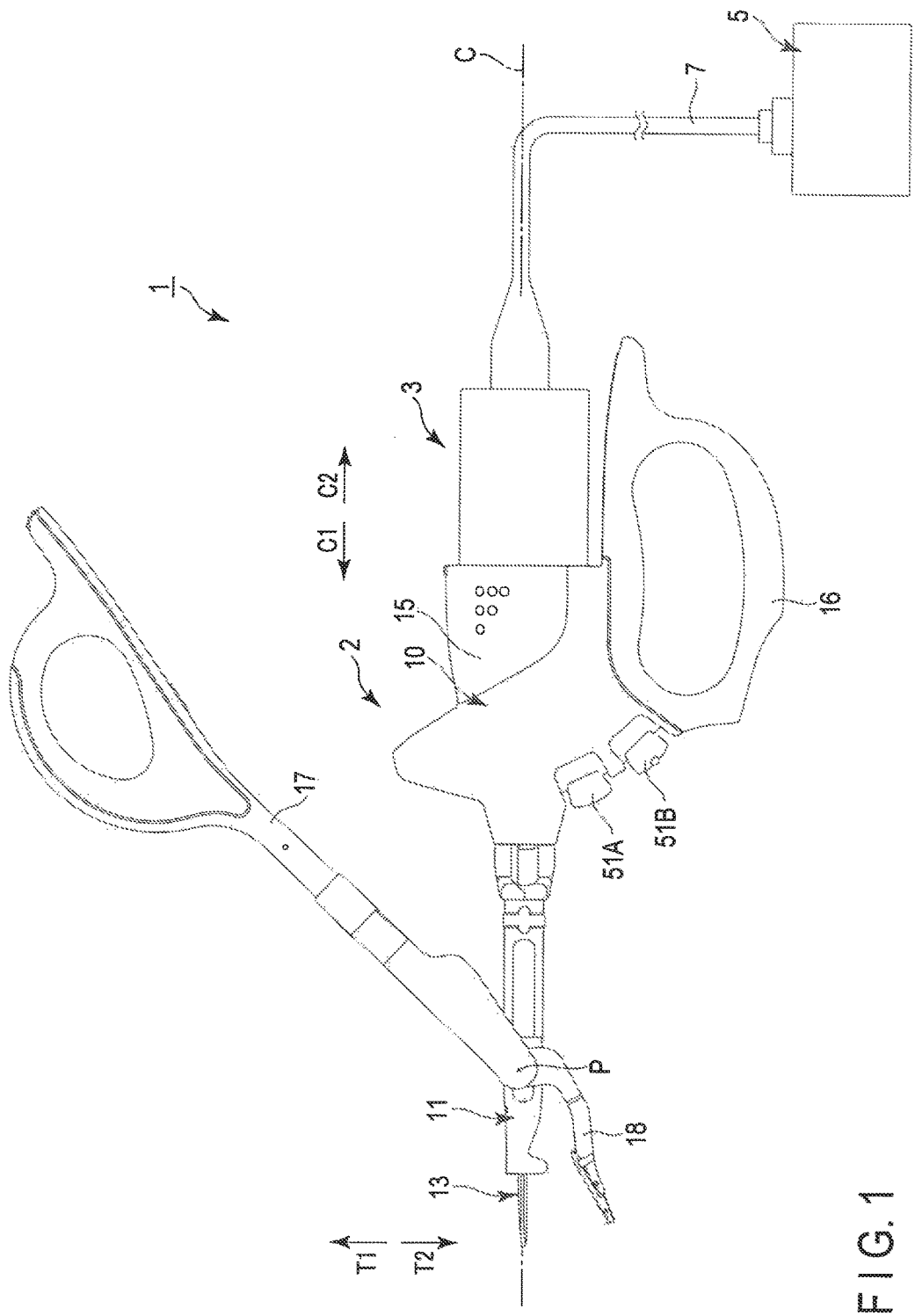
FIG. 1 is a schematic view illustrating a surgical treatment system according to a first embodiment.

FIG. 1 is a view illustrating a surgical treatment system 1 according to the present embodiment. As illustrated in FIG. 1, the surgical treatment system 1 includes a surgical treatment instrument 2, a transducer unit 3 and an energy source unit 5. The surgical treatment instrument 2 has a longitudinal axis C. Here, a direction parallel to the longitudinal axis C is defined as a longitudinal axial direction. One side in the longitudinal axial direction is a distal side (arrow C1 side in FIG. 1), and a side opposite to the distal side is a proximal side (arrow C2 side in FIG. 1). In the present embodiment, the surgical treatment instrument 2 treats a treated target, such as a biological tissue, by using ultrasonic vibration and high-frequency electric power (high-frequency electric energy). Accordingly, the surgical treatment instrument 2 is an ultrasonic treatment instrument and is also a high-frequency treatment instrument (bipolar treatment instrument).

The energy source unit 5 is, for example, an energy control device, and includes an electric power source and an amplifier circuit (both not shown). In addition, the energy source unit 5 includes a controller (not shown) which is composed of a processor including a CPU (Central Processing Unit) or an ASIC (application specific integrated circuit), and a storage section such as a memory. In the energy source unit 5, high-frequency electric power (high-frequency electric energy) and vibration generating electric power (vibration generating electric energy) are generated based on electric power from the electric power source. Besides, one end of a cable 7 is connected to the transducer unit 3. The other end of the cable 7 is detachably connected to the energy source unit 5.

The surgical treatment instrument 2 includes a held unit 10, a sheath 11 and a probe (rod) 13. The held unit 10 includes a held main body 15 which extends in the longitudinal axial direction (along the longitudinal axis C), and a stationary handle 16 which is formed integral with the held main body 15. The sheath 11 is formed of a metallic material, and has electrical conductivity. In addition, the probe 13 is formed of a material with high vibration transmissivity, such as a titanium alloy, and has electrical conductivity. The sheath 11 and probe 13 extend in the longitudinal axial direction, and are coupled to the held unit 10 in the state in which the sheath 11 and probe 13 are inserted in the inside of the held main body 15 from the distal side. Furthermore, the transducer unit 3 is detachably coupled to the held unit 10 in the state in which the transducer unit 3 is inserted in the inside of the held main body 15 from the proximal side.

In addition, the surgical treatment instrument 2 includes a movable handle 17 and a jaw 18. The movable handle 17 and jaw 18 are supported on a distal portion of the sheath 11, and are rotatable as one piece, relative to the held unit 10, sheath 11 and probe 13. The movable handle 17 and jaw 18 rotate about a rotational axis P which passes through a support position at which the movable handle 17 and jaw 18 are supported on the sheath 11, and extends along a direction crossing (perpendicular to) the longitudinal axis C. Here, one side of a direction, which crosses (is perpendicular to) the longitudinal axis C and is perpendicular to the rotational axis P, is defined as a first crossing direction (direction of arrow T1 in FIG. 1), and a side opposite to the first crossing direction is defined as a second crossing direction (direction of arrow T2 in FIG. 1). In the present embodiment, the stationary handle 16 is located on the second crossing direction side with respect to the longitudinal axis C. By the movable handle 17 and jaw 18 rotating, the movable handle 17 opens toward the first crossing direction (first perpendicular direction) relative to the held unit 10 (stationary handle 16), or closes toward the second crossing direction (second perpendicular direction) relative to the held unit 10. In addition, by the movable handle 17 and jaw 18 rotating, the jaw 18 opens toward the second crossing direction relative to the distal portion of the probe 13, or closes toward the first crossing direction relative to the distal portion of the probe 13.

Figure 2:
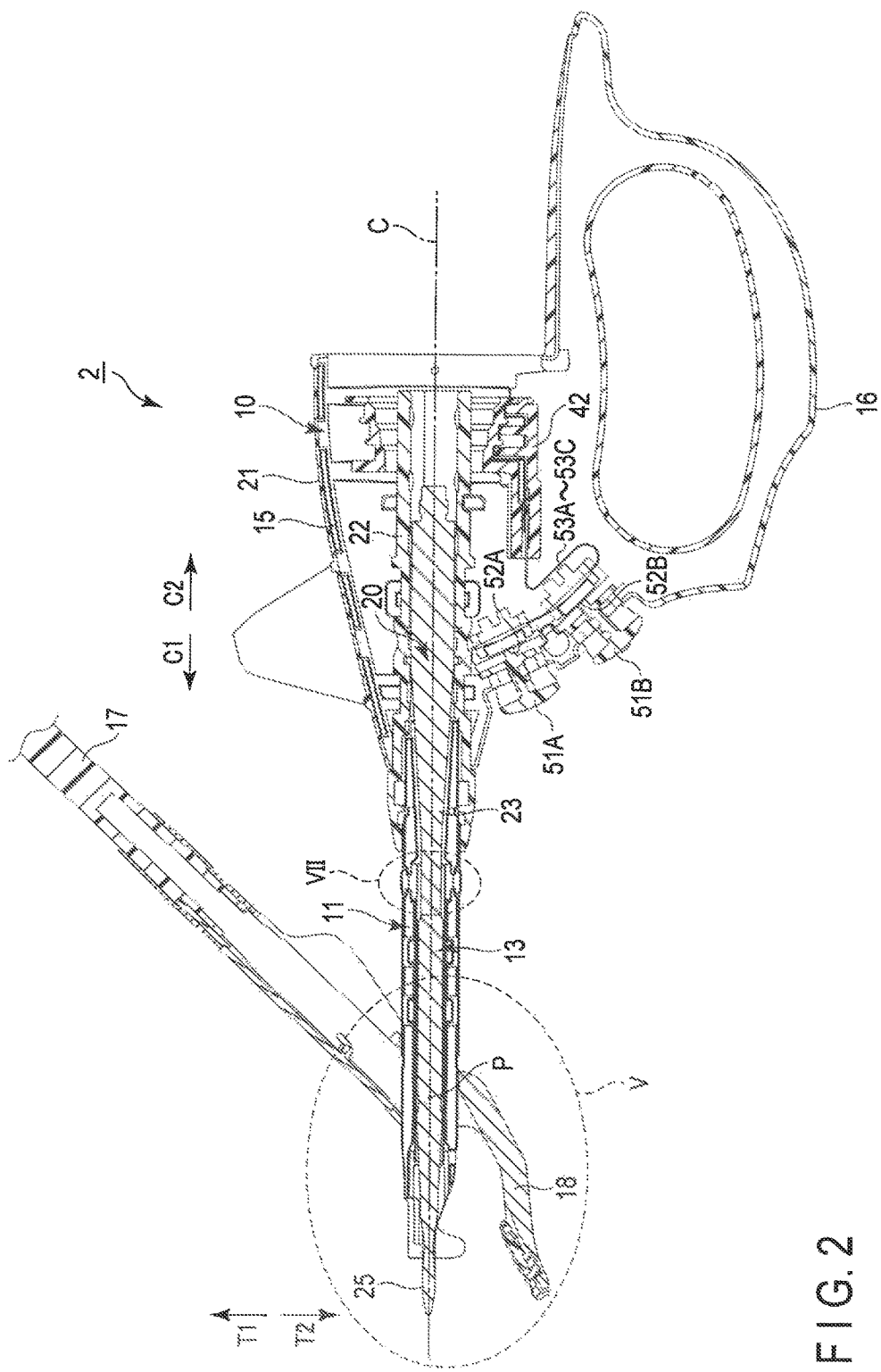
FIG. 2 is a cross-sectional view which schematically illustrates, in cross section perpendicular to a rotational axis of a jaw, a surgical treatment instrument according to the first embodiment.
Figure 4:
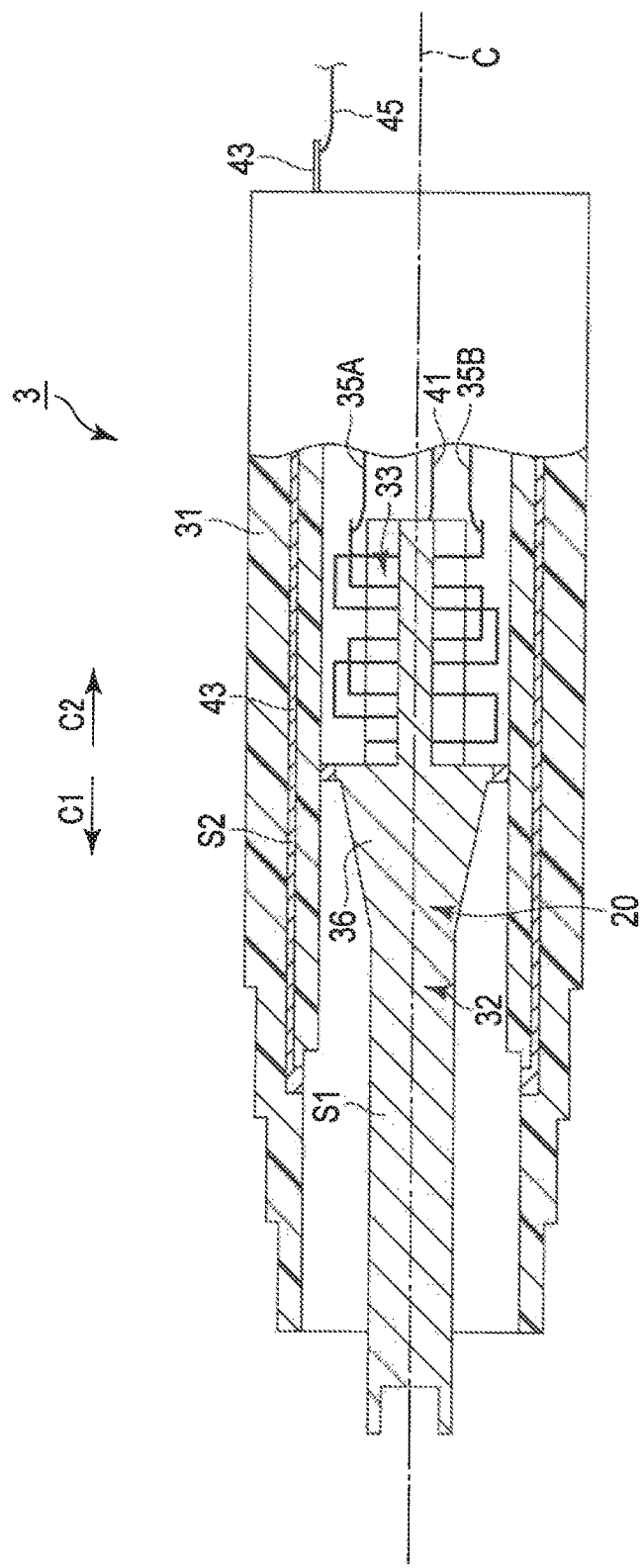
FIG. 4 is a cross-sectional view which schematically illustrates a transducer unit according to the first embodiment.

FIG. 2 and FIG. 3 are views illustrating the surgical treatment instrument 2. FIG. 2 illustrates a cross section perpendicular to the rotational axis P of the movable handle 17 and jaw 18, and FIG. 3 illustrates a cross section perpendicular to the first crossing direction and second crossing direction. Besides, FIG. 4 is a view illustrating the transducer unit 3. As illustrated in FIG. 2 and FIG. 3, the held unit 10 includes a held casing 21 which forms an armor of the held main body 5, and a connection cylindrical member 22 which is coupled to the held casing 21. The connection cylindrical member 22 extends in the longitudinal axial direction (along the longitudinal axis C), and is inserted in the inside of the held casing 21 from the distal side. In addition, the connection cylindrical member 22 is formed of an insulative material (e.g. a metallic material or plastic material having electrical insulation and heat resistance), and forms a part of the outer surface of the held main body 15.

The sheath 11 is coupled to the connection cylindrical member 22 in the state in which the sheath 11 is inserted in the inside of the connection cylindrical member 22 from the distal side. The probe 13 includes a proximal end and a distal end, and extends toward the distal side from the inside of the connection cylindrical member 22 through the inside of the sheath 11. The probe 13 includes a probe main body 23, and a probe treatment portion 25 which is continuous with the distal side of the probe main body 23. The probe main body 23 extends along the longitudinal axis C, with the longitudinal axis C being the center axis. The probe 13 is inserted through the sheath 11 in the state in which the probe treatment portion 25 (probe distal portion) projects from the distal end of the sheath 11. In addition, the probe treatment portion 25 includes a probe curved portion 26 which curves relative to the longitudinal axis C. In the present embodiment, the probe curved portion 26 curves relative to the longitudinal axis C, toward one side of a direction that is parallel to the rotational axis P. Specifically, the probe curved portion 26 curves toward one certain direction which crosses (is perpendicular to) the longitudinal axis C. In addition, the jaw 18 also curves in accordance with the probe treatment portion 25 (probe curved portion 26), and is opposed to the probe treatment portion 25.

As illustrated in FIG. 4, the transducer unit 3 includes a transducer case 31 which forms an armor, and a rod-shaped member (vibration transmission member) 32 which is attached to the transducer case 31. The rod-shaped member 32 is supported by the transducer case 31 in the inside of the transducer case 31. In addition, in the state in which the transducer unit 3 is coupled to the held unit 10, the rod-shaped member 32 extends along the longitudinal axis C. An ultrasonic transducer 33, which is a vibration generator, is attached to the rod-shaped member 32. The ultrasonic transducer 33 is provided with piezoelectric elements which convert an electric current to ultrasonic vibration. One end of each of electrical wiring lines 35A and 35B is connected to the ultrasonic transducer 33. The electrical wiring lines 35A and 35B extend through the inside of the cable 7, and the other ends thereof are connected to the energy source unit 5. In addition, in the rod-shaped member 32, a horn portion 36 is formed on the distal side with respect to the ultrasonic transducer 33. In the horn portion 36, the cross-sectional area perpendicular to the longitudinal axis C decrease gradually toward the distal side.

In the state in which the transducer unit 3 is coupled to the held unit 10 (surgical treatment instrument 2), the rod-shaped member 32 is inserted into the inside of the connection cylindrical member 22 from the proximal side. In addition, the probe 13 is connected to the distal side of the rod-shaped member 32 in the inside of the connection cylindrical member 22. Specifically, a distal end of the rod-shaped member 32 is connected to a proximal end of the probe 13. Vibration generating electric power (vibration generating electric energy) is generated by the energy source unit 5, and thereby the vibration generating electric power is supplied to the ultrasonic transducer 33 from the energy source unit 5 via the electrical wiring lines 35A and 35B. Thereby, electric current is converted to ultrasonic vibration by the ultrasonic transducer 33, and the ultrasonic vibration is generated. Then, the generated ultrasonic vibration is transmitted to the probe 13 through the rod-shaped member 32. Further, in the probe 13, the ultrasonic vibration is transmitted to the probe treatment portion 25 from the proximal side toward the distal side. By the probe treatment portion 25 vibrating by the ultrasonic vibration, a treated target, such as a biological tissue, which is grasped between the jaw 18 and probe treatment portion 25, is coagulated and, at the same time, cut and opened by frictional heat.

At this time, a vibrating body unit 20, which vibrates in a predetermined vibration state, is formed by the probe 13, rod-shaped member 32 and ultrasonic transducer 33. By the vibrating body unit 20 vibrating in the predetermined vibration state by the ultrasonic vibration, the vibrating body unit 20 including the probe 13 performs longitudinal vibration at a predetermined resonance frequency (e.g. 47 kHz), with the vibrating direction being parallel to the longitudinal axial direction. In the state in which the vibrating body unit 20 vibrates in the predetermined vibration state, one of vibration anti-nodes A of ultrasonic vibration is located at the distal end of the vibrating body unit 20 (the distal end of the probe 13), and another one of the vibration anti-nodes A of ultrasonic vibration is located at the proximal end of the vibrating body unit 20 (the proximal end of the rod-shaped member 32). In addition, in the state in which the vibrating body unit 20 vibrates in the predetermined vibration state, the number of vibration anti-nodes A and nodes N existing in the vibrating body unit 20, and the positions of the respective anti-nodes A and nodes N in the longitudinal axial direction are fixed.

As illustrated in FIG. 4, one end of an electrical wiring line 41 is connected to the rod-shaped member 32. The electrical wiring line 41 extends through the inside of the cable 7, and the other end thereof is connected to the energy source unit 5. High-frequency electric power (high-frequency electric energy) is generated by the energy source unit 5, and thereby the high-frequency electric power is supplied to the probe treatment portion 25 through the electrical wiring line 41, rod-shaped member 32 and probe 13. Thereby, the probe treatment portion 25 functions as one of electrodes of high-frequency electric power. Specifically, a probe-side supply path S1 of high-frequency electric power is formed by the electrical wiring line 41, rod-shaped member 32 and probe 13.

As illustrated in FIG. 2 and FIG. 3, a relay ring member 42 is provided in the inside of the held main body 15 in the state in which the relay ring member 42 is fixed to the held casing 21. The relay ring member 42 is disposed in such a state as to cover the entire periphery of a proximal portion of the connection cylindrical member 22. A gap is formed in the radial direction between the relay ring member 42 and the connection cylindrical member 22. In the state in which the transducer unit 3 is coupled to the held unit 10, the transducer case 31 is inserted between the relay ring member 42 and connection cylindrical member 22, and the connection cylindrical member 22 is connected to the distal side of the transducer case 31.

As illustrated in FIG. 4, a case conductive portion 43 is formed in the transducer case 31. One end of an electrical wiring line 45 is connected to the case conductive portion 43. The electrical wiring line 45 extends through the inside of the cable 7, and the other end thereof is connected to the energy source unit 5.

In addition, as illustrated in FIG. 3, conductive plates 47A and 47B, which are formed of a metal or the like, are attached to the outer peripheral surface of the connection cylindrical member 22. A proximal portion of each of the conductive plates 47A and 47B is inserted between the relay ring member 42 and connection cylindrical member 22. In the state in which the transducer unit 3 is coupled to the held unit 10, a distal portion of the case conductive portion 43 of the transducer case 31 comes in contact with the proximal portion of the conductive plates 47A and 47B. In addition, distal portions of the conductive plates 47A and 47B abut on the sheath 11. In addition, the sheath 11 and jaw 18 are electrically connected via an attachment position of the jaw 18 to the sheath 11.

High-frequency electric power is generated by the energy source unit 5, and thereby the high-frequency electric power is supplied to a conductive portion (not shown) of the jaw 18 through the electrical wiring line 45, the case conductive portion 43 of the transducer case 31, the conductive plates 47A and 47B and the sheath 11. Thereby, the conductive portion of the jaw 18 functions as the other electrode of high-frequency electric power. Specifically, a jaw-side supply path S2 of high-frequency electric power is formed by the electrical wiring line 45, case conductive portion 43, conductive plates 47A and 47B and sheath 11. Incidentally, the probe-side supply path S1 and jaw-side supply path S2 are configured not to come in contact.

High-frequency electric power is supplied to the jaw 18 and probe treatment portion 25, and thereby a voltage (electric potential difference) occurs between the jaw 18 and probe treatment portion 25. Thereby, if a treated target is grasped between the jaw 18 and probe treatment portion 25, a high-frequency current is passed through the treated target. By the high-frequency current, the treated target is denatured, and coagulation is promoted. In addition, a coating is applied to the exposed surface of the sheath 11, which is exposed to the outside. This coating is an insulating coating or a water-repellent coating. In the case of the insulating coating, discharge of high-frequency current from the exposed surface of the sheath 11 can effectively be prevented even when the exposed surface of the sheath 11 came in contact with a biological tissue or the like, other than the treated target.

FIG. 5 is a view illustrating, in enlarged scale, a region V in FIG. 2. The jaw 18 is provided with an abutment surface 48. When the movable handle 17 and jaw 18 are rotated and the jaw 18 is opened relative to the probe treatment portion 25 (the distal portion of the probe 13), the abutment surface 48 abuts on that part of the exposed surface of the sheath 11, which faces in the second crossing direction. By the abutment surface 48 abutting on the exposed surface of the sheath 11, the movement of the jaw 18 in the second crossing direction (opening direction) is restricted, and the movement of the movable handle 17 in the first crossing direction (opening direction) is restricted. Thus, when the abutment surface 48 abuts on the exposed surface of the sheath 11, the state of maximum opening of the jaw 18 is defined. At this time, since the abutment surface 48 comes in surface-contact with the external exposed surface of the sheath 11, the area of contact between the abutment surface 48 and sheath 11 increases, and the load acting on the sheath 11 from the abutment surface 48 does not increase. Thus, peeling of the external insulating coating of the sheath 11, which occurs due to the abutment of the abutment surface 48 upon the exposed surface of the sheath, can effectively be prevented.

In addition, as illustrated in FIG. 3, the radial distance between each conductive plate 47A, 47B and the vibrating body unit 20 (probe 13), which vibrates by ultrasonic vibration, is small. Thus, the resonance frequency of each conductive plate 47A, 47B is set to a value which deviates from a predetermined resonance frequency (e.g. 47 kHz) in the state in which the vibrating body unit 20 vibrates in the predetermined vibration state. Specifically, the vibration characteristic of each conductive plate 47A, 47B is set in such a state that the conductive plate 47A, 47B does not vibrate at the predetermined resonance frequency at a time when the vibrating body unit 20 vibrates in the predetermined vibration state. In each conductive plate 47A, 47B, the resonance frequency (vibration characteristic) is adjusted by adjusting at least one of the shape, the position of abutment on the connection cylindrical member 22 and sheath 11, and the quality of material (Young's modulus). Since each conductive plate 47A, 47B has such a vibration characteristic as not to vibrate at the predetermined resonance frequency at a time when the vibrating body unit 20 vibrates, the occurrence of noise can effectively be prevented in the state in which the vibrating body unit 20 vibrates in the predetermined vibration state. In the meantime, aside from the conductive plate 47A, 47B, members, which have small distances from the vibrating body unit 20, may have such a vibration characteristic as not to vibrate at the predetermined resonance frequency at a time when the vibrating body unit 20 vibrates.

As illustrated in FIG. 2, energy operation buttons 51A and 51B, which are energy operation input portions, are attached to the held casing 21. In addition, switches 52A and 52B are provided in the inside of the held casing 21. The open or closed state of the switch 52A changes based on an input of an energy operation in the energy operation button 51A, and the open or closed state of the switch 52B changes based on an input of an energy operation in the energy operation button 51B. The switches 52A and 52B are connected to the relay ring member 42 via electrical wiring lines 53A to 53C. The switches 52A and 52B are electrically connected to the energy source unit 5 via detection circuitry (not shown) formed in the inside of the held casing 21 (specifically, the electrical wiring lines 53A to 53C and relay ring member 42), in the transducer case 31 and in the inside of the cable 7. The energy source unit 5 detects the open or closed state of each of the switches 52A and 52B via the detection circuitry, thereby detecting the presence or absence of the input of the energy operation in the corresponding energy operation button (51A or 51B). If the input of the energy operation in the energy operation button 51A is detected, the energy source unit 5 generates and outputs vibration generating electric power and high-frequency electric power. Then, as described above, ultrasonic vibration is transmitted to the probe treatment portion 25, and high-frequency electric power is supplied to the probe treatment portion 25 and jaw 18. In addition, if the input of the energy operation in the energy operation button 51B is detected, the energy source unit 5 generates only high-frequency electric power, and the high-frequency electric power is supplied to the probe treatment portion 25 and jaw 18. At this time, vibration generating electric power is not output, and no ultrasonic vibration occurs. In the meantime, the detection circuitry is electrically insulated from the above-described probe-side supply path S1 and jaw-side supply path S2.

Figure 7:
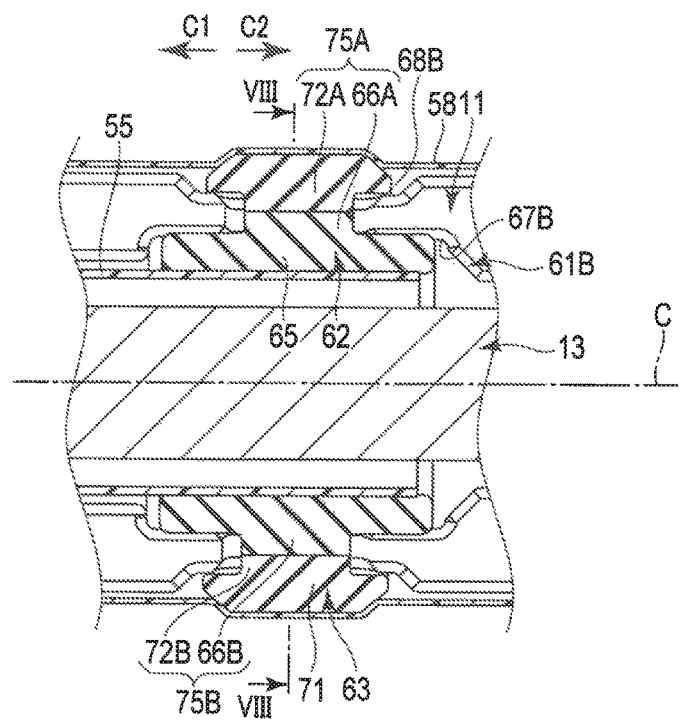
FIG. 7 is a cross-sectional view illustrating, in enlarged scale, a region VII in FIG. 2.

FIG. 6 is an exploded view illustrating respective parts of a configuration located on a distal side with respect to the held unit 10, with the movable handle 17 and jaw 18 being omitted. In addition, FIG. 7 is a view illustrating, in enlarged scale, a region VII in FIG. 2. As illustrated in FIG. 5 to FIG. 7, an inner tube 55 extends in the longitudinal axial direction (along the longitudinal axis C) between the sheath 11 and probe 13 in the radial direction. The inner tube 55 is formed of a hard resin with electrical insulation, and is formed of, for example, PEEK (polyether ether ketone). The probe 13 is inserted through the inner tube 55. In addition, a distal end of the inner tube 55 is located on the proximal side with respect to the distal end of the sheath 11, and a proximal end of the inner tube 55 is located on the distal side with respect to the proximal end of the sheath 11. Accordingly, the inner tube 55 is located in the inside of the sheath 11 over the entire length in the longitudinal axial direction.

An annular intervening portion 56 is provided between the probe 13 and the inner tube 55 in the radial direction. The intervening portion 56 is formed of an elastic material, and is insert-formed on an outer peripheral surface of the probe 13 in the present embodiment. In addition, the intervening portion 56 may be an annular member which is formed of an elastic material and is a separate body from the probe 13.

The inner tube 55 supports the probe 13 via the intervening portion 56. By the intervening portion 56, liquid-tightness is kept between the probe 13 and the inner tube 55. Thus, even if liquid enters between the probe 13 and inner tube 55 from the distal side, the flow of the liquid to the proximal side from the intervening portion 56 is prevented between the probe 13 and inner tube 55.

In addition, in the state in which the vibrating body unit 20 including the probe 13 vibrates in the predetermined vibration state, a vibration node N1, which is one of the vibration nodes N of ultrasonic vibration, is located at a position which is not spaced apart from the intervening portion 56 in the longitudinal axial direction. Specifically, in the state in which the vibrating body unit 20 vibrates in the predetermined vibration state, the position at which the probe 13 is supported via the intervening portion 56 is the vibration node N1 of ultrasonic vibration. Thus, in the state in which the vibrating body unit 20 vibrates in the predetermined vibration state, ultrasonic vibration is not transmitted from the probe 13 to the inner tube 55 via the intervening portion 56.

Figure 8:
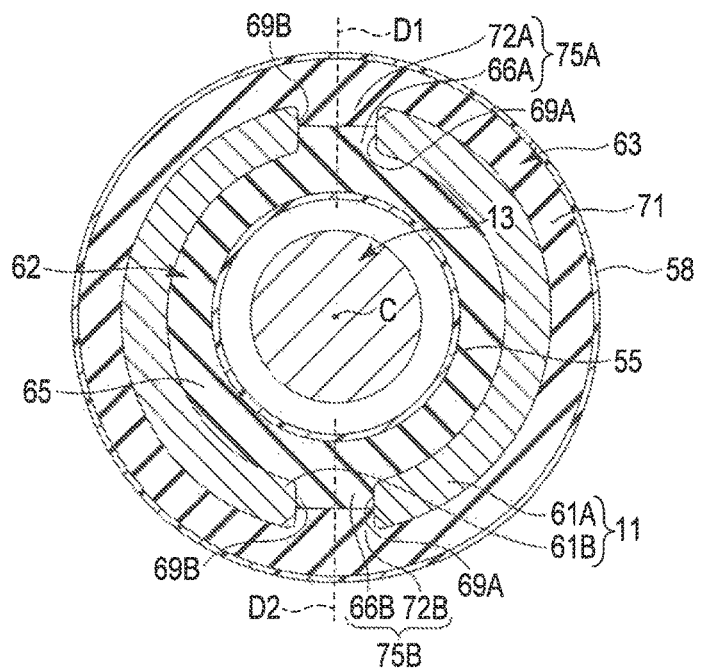
FIG. 8 is a cross-sectional view taken along line VIII-VIII in FIG. 7.

FIG. 8 is a cross-sectional view taken along line VIII-VIII in FIG. 7. As illustrated in FIG. 5 to FIG. 8, the sheath 11 is formed of a plurality (two in this embodiment) of sheath components 61A and 61B. The sheath component (first sheath component) 61A is divided (cut) from the sheath component (second sheath component) 61B at a dividing plane (cutting plane) D1, D2 that is along the longitudinal axial direction (parallel to the longitudinal axial direction). Specifically, each sheath component 61A, 61B is divided at the dividing plane D1, D2 from the sheath component (61A or 61B) that neighbors in the circumferential direction. In the present embodiment, the dividing plane (engaging plane) D1, D2 is perpendicular to the rotational axis P of the jaw 18. In addition, in the present embodiment, the dividing planes (divided parts) D1 and D2 are spaced apart by about 180° in the circumferential direction (a direction about the longitudinal axis). The cylindrical sheath 11 is formed by engaging the sheath component 61A with the sheath component 61B in such a state that the sheath component 61A is properly abutted on the sheath component 61B at the respective dividing planes (engaging planes) D1 and D2.

On the outer peripheral side of the sheath 11, an outer tube 58 extends in the longitudinal direction (along the longitudinal axis C). The outer tube 58 is formed of a resin such as a rubber material, which has electrical insulation and expands or contracts in the radial direction. The sheath 11 is inserted through the outer tube 58. Accordingly, the distal end of the sheath 11 is located on the distal side with respect to the distal end of the outer tube 58, and the proximal end of the sheath 11 is located on the proximal side with respect to the proximal end of the outer tube. The outer tube 58 is coupled to the connection cylindrical member 22 in the state in which the outer tube 58 is inserted into the inside of the connection cylindrical member 22 from the distal side. In addition, an abutment part of the abutment surface 48 of the jaw 18, which abuts on the sheath 11, is located on the distal side with respect to the outer tube 58.

In addition to the inner tube 55 and sheath 11, an inner elastic member (first elastic member) 62 and an outer elastic member (second elastic member) 63 are provided between the outer tube 58 and probe 13 in the radial direction. Each of the inner elastic member (first elastic member) 62 and outer elastic member (second elastic member) 63 has an annular shape or a cylindrical shape. In the present embodiment, the inner elastic member 62 and outer elastic member 63 are located on the proximal side with respect to the intervening portion 56 which is disposed on the outer periphery of the probe 13.

An inner engaging portion (67A or 67B) is provided on the inner peripheral surface of each sheath component 61A, 61B. The inner engaging portions 67A and 67B cooperate to set a position of the inner elastic member 62 in the longitudinal direction. In addition, the outer peripheral surface of each sheath component 61A, 61B is provided with an outer engaging portion (68A or 68B). The outer engaging portions 68A and 68B cooperate to set a position of the outer elastic member 63 in the longitudinal direction. Recess portions 69A and 69B are provided at the dividing planes D1 and D2 of the sheath components 61A and 61B. At the dividing planes D1 and D2, the recess portions 69A and 69B cooperate to prevent the inner elastic member 62 and outer elastic member 63 from rotating in the circumferential direction about the longitudinal axis C. At the dividing planes D1 and D2, the recess portions 69A and 69B are recessed in the circumferential direction from the abutment surface at which the sheath components 61A and 61B abut on each other, and the recess portions 69A and 69B are spaced apart from each other in the circumferential direction. Incidentally, only one of the recess portions 69A and 69B may be formed.

The inner elastic member 62 and outer elastic member 63 are not spaced apart from each other in the longitudinal axial direction. Specifically, the outer elastic member 63 is provided on the outside of the inner elastic member 62. Accordingly, the inner elastic member 62 and outer elastic member 63 are located at substantially the same position in the longitudinal axial direction. Incidentally, FIG. 8 illustrates a cross section which is perpendicular to the longitudinal axis C and passes through the inner elastic member 62 and outer elastic member 63.

The inner elastic member 62 includes an annular inner seal portion (first seal portion) 65 which is provided between the inner tube 55 and sheath 11 in the radial direction. By the inner seal portion 65, liquid-tightness is kept between the inner tube 55 and sheath 11. Specifically, the inner peripheral surface of the inner seal portion 65 of the inner elastic member 62 is put in close contact with the outer peripheral surface of the inner tube 55, and the outer peripheral surface of the inner seal portion 65 is put in close contact with the inner peripheral surfaces of the sheath components 61A and 61B. Thus, sealing is effected annularly between the inner tube 55 and sheath 11. Even if liquid flows in from the distal side, the liquid is prevented from entering toward the proximal side from the inner seal portion 65 between the sheath 11 and inner tube 55. Specifically, the inner seal portion (first seal portion) 65 is provided between the sheath 11 and probe 13 in the radial direction, and prevents the flow of liquid to the proximal side in the inside of the sheath 11.

In addition, the inner elastic member 62 includes inner projection portions (first projection portions) 66A and 66B (two inner projection portions in this embodiment) which project from the outer peripheral surface of the inner seal portion 65 toward the outer peripheral side. The inner projection portions 66A and 66B are spaced apart by about 180° in the circumferential direction. The inner projection portion 66A projects toward the divided part (engaging part) D1 between the sheath component 61A and sheath component 61B, and is clamped between the recess portion (recessed end face) 69A of the sheath component 61A and the recess portion (recessed end face) 69B of the sheath component 61B at the divided part D1. In addition, the inner projection portion 66B projects toward the divided part (engaging part) D2 between the sheath component 61A and sheath component 61B, and is clamped between the recess portion (recessed end face) 69A of the sheath component 61A and the recess portion (recessed end face) 69B of the sheath component 61B at the divided part D2. Specifically, partial separation is made at each dividing plane (end face) D1, D2 of the sheath components 61A and 61B. In addition, at each dividing plane (end face) D1, D2 of the sheath components 61A and 61B, the corresponding inner projection portion (66A or 66B) of the inner elastic member 62 is disposed in a state of close contact between the recess portions 69A and 69B which are spaced apart.

The outer elastic member 63 includes an annular outer seal portion (third seal portion) 71 which is provided on the outer peripheral side of the sheath 11 in such a state as to cover the entire periphery of the sheath 11. The outer seal portion 71 is located between the outer tube 58 and sheath 11 in the radial direction. By the outer seal portion 71, liquid-tightness is kept between the outer tube 58 and sheath 11. Specifically, the inner peripheral surface of the outer seal portion 71 of the outer elastic member 63 is put in close contact with the outer peripheral surface of the sheath component 61A, 61B, and the outer peripheral surface of the outer seal portion 71 is put in close contact with the inner peripheral surface of the outer tube 58. Thus, sealing is effected annularly between the outer tube 58 and sheath 11. Even if liquid flows in from the distal side, the liquid is prevented from entering toward the proximal side from the outer seal portion 71 between the sheath 11 and outer tube 58. Specifically, the outer seal portion (third seal portion) 71 prevents the flow of liquid to the proximal side on the outer peripheral side of the sheath 11. In addition, since the inner elastic member 62 and outer elastic member 63 are not spaced apart from each other in the longitudinal axial direction, the outer seal portion 71 is provided at a position which is not spaced apart from the inner seal portion 65 in the longitudinal axial direction. Accordingly, the inner seal portion (first seal portion) 65 and outer seal portion (third seal portion) 71 are located at substantially the same position in the longitudinal axial direction.

Furthermore, the outer elastic member 63 includes outer projection portions (second projection portions) 72A and 72B (two outer projection portions in this embodiment) which project from the inner peripheral surface of the outer seal portion 71 toward the inner peripheral side. The outer projection portions 72A and 72B are spaced apart by about 180° in the circumferential direction. The outer projection portion 72A projects toward the divided part (engaging part) D1 between the sheath component 61A and sheath component 61B, and is clamped between the recess portion (recessed end face) 69A of the sheath component 61A and the recess portion (recessed end face) 69B of the sheath component 61B at the divided part D1. In addition, at the divided part (engaging part) D1, a projection end (inner end) of the outer projection portion 72A is in close contact with a projection end (outer end) of the inner projection portion 66A. Besides, the outer projection portion 72B projects toward the divided part (engaging part) D2 between the sheath component 61A and sheath component 61B, and is clamped between the recess portion (recessed end face) 69A of the sheath component 61A and the recess portion (recessed end face) 69B of the sheath component 61B at the divided part D2. In addition, at the divided part (engaging part) D2, a projection end (inner end) of the outer projection portion 72B is in close contact with a projection end (outer end) of the inner projection portion 66B. Specifically, as described above, since partial separation is made at each dividing plane (end face) D1, D2 of the sheath components 61A and 61B, the corresponding outer projection portion (72A or 72B) of the outer elastic member 63 is disposed in a state of close contact between the recess portions 69A and 69B which are spaced apart. In addition, the inner projection portion 66A of the inner elastic member 62 and the outer projection portion 72A of the outer elastic member 63 are put in close contact, and the inner projection portion 66B of the inner elastic member 62 and the outer projection portion 72B of the outer elastic member 63 are put in close contact.

In the present embodiment, a relay seal portion (second seal portion) 75A, which keeps the divided part D1 liquid-tight, is formed by the inner projection portion 66A of the inner elastic member 62 and the outer projection portion 72A of the outer elastic member 63. In addition, in this embodiment, a relay seal portion (second seal portion) 75B, which keeps the divided part D2 liquid-tight, is formed by the inner projection portion 66B of the inner elastic member 62 and the outer projection portion 72B of the outer elastic member 63. Specifically, each of the divided parts (D1 and D2) of the sheath component 61A from the adjacent sheath component 61B is kept liquid-tight by the corresponding relay seal portion (75A or 75B). Thus, even when liquid flowed in from the distal side to each divided part D1, D2, the liquid is prevented from entering toward the proximal side from the corresponding relay seal portion (75A or 75B) at each divided part D1, D2.

Since the inner elastic member 62 and outer elastic member 63 are not spaced apart from each other in the longitudinal axial direction, the relay seal portion 75A, 75B is provided at a position which is not spaced apart from the inner seal portion 65 and outer seal portion 71 in the longitudinal axial direction. Accordingly, the relay seal portion (second seal portion) 75A, 75B is located at substantially the same position in the longitudinal axial direction as the inner seal portion (first seal portion) 65 and outer seal portion (third seal portion) 71. In addition, each relay seal portion 75A, 75B is formed in such a state as to project from the outer peripheral surface of the inner seal portion (first seal portion) 65 toward the corresponding divided part (D1 or D2). Furthermore, each relay seal portion 75A, 75B is formed in such a state as to project from the inner peripheral surface of the outer seal portion (third seal portion) 71 toward the corresponding divided part (D1 or D2).

In the above-described configuration, a pushing force toward the inner peripheral side acts on the inner tube 55 via the inner seal portion 65. Here, the inner tube 55 is formed of a hard resin. Thus, in the state in which the pushing force toward the inner peripheral side acts on the inner tube 55, the inner tube 55 does not come in contact with the probe 13 at a position different from the intervening portion 56 in the longitudinal axial direction. Specifically, the inner tube 55 is held in a state of non-contact with the probe 13 at a position other than the intervening portion 56.

Additionally, in the state in which the vibrating body unit 20 vibrates in the predetermined vibration state, each of the vibration nodes N of ultrasonic vibration is spaced apart from the first elastic member 62 and second elastic member 63 in the longitudinal axial direction. Specifically, the vibration nodes N of ultrasonic vibration in the state in which the vibrating body unit 20 vibrates in the predetermined vibration state are located apart from the inner seal portion (first seal portion) 65, relay seal portion (second seal portion) 75A, 75B and outer seal portion (third seal portion) 71 in the longitudinal axial direction. Thus, in the state in which the vibrating body unit 20 vibrates in the predetermined vibration state, the position on the cross section (e.g. the cross section of FIG. 8) in the probe 13, which is perpendicular to the longitudinal axis C and passes through the first elastic member 62 and second elastic member 63, is not the vibration node of ultrasonic vibration, and longitudinal vibration occurs by ultrasonic vibration.

Additionally, as illustrated in FIG. 6, the outer elastic member 63 is provided with an engaging projection portion 81A which projects toward the distal side from the outer seal portion (third seal portion) 71, and an engaging projection portion 81B which projects toward the proximal side from the outer seal portion 71. The engaging projection portions 81A and 81B are located at substantially the same angular position in the circumferential direction (the direction about the longitudinal axis). Besides, the outer peripheral surface of the sheath component 61A or 61B of the sheath 11 is provided with an engaging groove 82A in which the engaging projection portion 81A can be engaged, and an engaging groove 82B in which the engaging projection portion 81B can be engaged. The engaging grooves 82A and 82B are formed in such a state as to be continuous with the outer engaging portions 68A and 68B of the sheath component 61A, 61B, and are located at substantially the same angular position in the circumferential direction. The outer elastic member 63 is attached to the outer peripheral surface of the sheath 11 in the state in which the inner peripheral surface of the outer seal portion 71 is engaged with the outer engaging portions 68A and 68B of the sheath components 61A and 61B, the engaging projection portion 81A is engaged with the engaging groove 82A, and the engaging projection portion 81B is engaged with the engaging groove 82B. Thereby, the outer elastic member 63 is set a position relative to the sheath 11 in the circumferential direction, in the state in which the outer projection portion 72A is inserted in the divided part D1 and the outer projection portion 72B is inserted in the divided part D2. Incidentally, the engaging projection portion 81A, 81B and the engaging groove 82A, 82B may not be provided.

In the meantime, the outer tube 58 is formed to be longer than the outer elastic member 63 in the longitudinal axial direction. The outer tube 58 holds the outer elastic member 63 from the outer periphery onto the sheath 11. The outer tube 58 includes an engaging groove 83 in which the outer peripheral surface of the outer seal portion 71 is engaged, and an engaging portion 84A, 84B in which the corresponding engaging projection portion (81A or 81B) is engaged.

Next, the function and advantageous effects of the surgical treatment instrument 2 of the present embodiment will be described. In this embodiment, the probe treatment portion 25 of the probe 13 is provided with the probe curved portion 26 which curves relative to the longitudinal axis C. Here, in this embodiment, the sheath 11 is divided into the sheath components 61A and 61B at the dividing plane D1, D2, which is parallel to the longitudinal axis C. Thus, at the time of manufacture, the assembly between the sheath 11 and the probe 13, which is inserted through the inside of the sheath 11, becomes easier. Thereby, even in the case in which the probe 13 is provided with the probe curved portion 26, the surgical treatment instrument 2 can easily be assembled.

When a treatment is performed by using the surgical treatment system 1 including the surgical treatment instrument 2, the sheath 11, probe 13 and jaw 18 are inserted into the body. Then, a treated target, such as a biological tissue, is disposed between the jaw 18 and probe treatment portion 25, and the movable handle 17 is closed relative to the held unit 10 (stationary handle 16). Thereby, the jaw 18 is closed relative to the probe treatment portion 25, and the treated target is grasped between the jaw 18 and probe treatment portion 25.

By an energy operation being input by the energy operation button 51A in the state in which the treated target is grasped, vibration generating electric power is supplied to the ultrasonic transducer 33 from the energy source unit 5 as described above, and ultrasonic vibration is generated. Then, the generated ultrasonic vibration is transmitted to the probe treatment portion 25 through the probe 13, and the treated target is coagulated and, at the same time, cut and opened by frictional heat occurring due to ultrasonic vibration. In addition, by the energy operation being input by the energy operation button 51A, high-frequency electric power is supplied to the probe treatment portion 25 and jaw 18 from the energy source unit 5. Thereby, as described above, the high-frequency current flows through the treated target, and the coagulation is promoted. Furthermore, by an energy operation being input by the energy operation button 51B in the state in which the treated target is grasped, high-frequency electric power is supplied to the probe treatment portion 25 and jaw 18 from the energy source unit 5. At this time, no ultrasonic vibration is generated.

Here, if the probe 13 is caused to vibrate in the state in which the probe treatment portion 25 is immersed in liquid, the liquid flows into the inside of the sheath 11 from the opening at the distal end of the sheath 11. The liquid, which has flowed in the inside of the sheath 11, flows into the inside of the inner tube 55 (i.e. between the inner tube 55 and probe 13) from the opening at the distal end of the inner tube 55. Here, liquid-tightness is kept annularly between the inner tube 55 and the probe 13 by the intervening portion 56. Thus, in the inside of the inner tube 55, the flow of liquid to the proximal side from the intervening portion 56 is prevented.

In addition, the liquid, which has flowed in the inside of the sheath 11, flows in between the inner tube 55 and sheath 11 from the distal end of the inner tube 55. Liquid-tightness is kept annularly between the outer peripheral surface of the inner tube 55 and the inner peripheral surface of the sheath 11 by the inner seal portion (first seal portion) 65 of the inner elastic member 62. Thus, the liquid, which has flowed in between the inner tube 55 and sheath 11, is prevented from flowing to the proximal side at the inner seal portion 65.

The liquid, which is prevented from flowing to the proximal side at the inner seal portion 65, flows to the outer peripheral side and flows into the divided parts D1 and D2 between the sheath component (first sheath component) 61A and the sheath component (second sheath component) 61B. At each divided part D1, D2, liquid-tightness is kept between the recess portions 69A and 69B by the corresponding relay seal portion (75A or 75B). Thus, the liquid, which has flowed into the divided parts D1 and D2 between the first sheath component 61A and second sheath component 61B, is prevented from flowing to the proximal side at the relay seal portion (second seal portion) 75A, 75B. Accordingly, in the present embodiment, even in the case in which the sheath 11 is divided into the plural sheath components 61A and 61B at the dividing plane (engaging plane) D1, D2, which is parallel to the longitudinal axis C, the relay seal portion (second seal portion) 75A, 75B can effectively prevent liquid from flowing toward the proximal side through the divided part (engaging part) D1, D2.

The liquid, which is prevented from flowing to the proximal side by the relay seal portion (second seal portion) 75A, 75B, flows out to the outer peripheral side and flows in between the sheath 11 and outer tube 58. Liquid-tightness is kept between the sheath 11 and outer tube 58 by the outer seal portion (third seal portion) 71 of the outer elastic member 63. Thus, the liquid, which has flowed in between the sheath 11 and outer tube 58, is prevented from flowing to the proximal side at the outer seal portion 71. Furthermore, since the outer tube 58 is provided, the liquid, which is prevented from flowing to the proximal side by the outer seal portion 71, is also prevented from flowing to the outer peripheral side.

Here, the inner seal portion (first seal portion) 65 and relay seal portion (second seal portion) 75A, 75B are not spaced apart from each other in the longitudinal axial direction, and are provided at substantially the same position in the longitudinal axial direction. Thus, the position in the longitudinal direction, at which the flow of liquid to the proximal side is prevented by the inner seal portion 65, substantially agrees with the position in the longitudinal direction, at which the flow of liquid to the proximal side is prevented by the relay seal portion 75A, 75B. Thereby, the flow toward the proximal side is prevented by the inner seal portion 65, and the liquid, which has flowed in the divided part D1, D2 of the sheath 11, does not re-flow in between the sheath 11 and inner tube 55 from the outer peripheral side.

Similarly, the relay seal portion (second seal portion) 75A, 75B and the outer seal portion (third seal portion) 71 are not spaced apart from each other in the longitudinal axial direction, and are provided at substantially the same position in the longitudinal axial direction. Thus, the position in the longitudinal axial direction, at which the flow of liquid to the proximal side is prevented by the relay seal portion 75A, 75B, substantially agrees with the position in the longitudinal direction, at which the flow of liquid to the proximal side is prevented by the outer seal portion 71. Thereby, the flow toward the proximal side is prevented by the relay seal portion 75A, 75B, and the liquid, which has flowed in between the sheath 11 and outer tube 58, does not re-flow in the divided part D1, D2 from the outer peripheral side.

In the present embodiment, since the inner seal portion (first seal portion) 65, relay seal portion (second seal portion) 75A, 75B and outer seal portion (third seal portion) 71 are not spaced apart from each other in the longitudinal axial direction, liquid-tightness is kept between the inner tube 55 and outer tube 58 by the inner seal portion 65, relay seal portion 75A, 75B and outer seal portion 71. Accordingly, the flow of liquid to the proximal side from, the position, where the inner seal portion 65, relay seal portion 75A, 75B and outer seal portion 71 are disposed, is prevented between the inner tube 55 and outer tube 58 in the radial direction.

As described above, in the present embodiment, even when liquid has flowed in the inside of the sheath 11 from the opening at the distal end of the sheath 11, the flow of the liquid toward the proximal side from the intervening portion 56 is prevented in the inside of the inner tube 55, and the flow of the liquid to the proximal side from the position, where the inner seal portion 65, relay seal portion 75A, 75B and outer seal portion 71 are disposed, is prevented between the inner tube 55 and outer tube 58. Thereby, the liquid, which has flowed in the inside of the sheath 11 from the distal end of the sheath 11, can effectively be prevented from flowing into the inside of the held unit 10. Since no liquid flows in the inside of the held unit 10, it is possible to effectively prevent short-circuit between the probe-side supply path S1 and jaw-side supply path S2 of high-frequency electric power via a liquid, for example, between the conductive plate 47A, 47B and probe main body 23. Since the short-circuit between the probe-side supply path S1 and jaw-side supply path S2 is prevented, high-frequency electric power is properly supplied to the probe treatment portion 25 and jaw 18, and a treatment can properly be performed by using the high-frequency electric power.

Additionally, in the state in which the vibrating body unit 20 including the probe 13 vibrates in the predetermined vibration state (at the predetermined resonance frequency), the vibration node N1 is located at a position which is not spaced apart from the intervening portion 56 in the longitudinal axial direction. Thus, in the state in which the vibrating body unit 20 vibrates in the predetermined vibration state, ultrasonic vibration is not transmitted from the probe 13 to the inner tube 55 via the intervening portion 56. In addition, the inner tube 55 is formed of a hard resin, and even if a pushing force toward the inner peripheral side acts on the inner tube 55, the inner tube 55 is held in a state of non-contact with the probe 13 at a position other than the intervening portion 56. Thus, no ultrasonic vibration is transmitted from the probe 13 via the position other than the intervening portion 56.

As described above, in the state in which the vibrating body unit 20 vibrates in the predetermined vibration state (at the predetermined resonance frequency), no ultrasonic vibration is transmitted from the probe 13 to the inner tube 55. Thus, ultrasonic vibration is not transmitted to the inner seal portion (first seal portion) 65, relay seal portion (second seal portion) 75A, 75B and outer seal portion (third seal portion) 71, and it is possible to effectively prevent the inner seal portion 65, relay seal portion 75A, 75B and outer seal portion 71 from being worn due to vibration.

Additionally, in the state in which the vibrating body unit 20 vibrates in the predetermined vibration state, the vibration nodes N of ultrasonic vibration are located apart from the inner seal portion 65, relay seal portion 75A, 75B and outer seal portion 71 in the longitudinal axial direction. For example, when the dimension of the probe 13 in the longitudinal direction is small and the number of vibration nodes N in the predetermined vibration state is small, there is a case in which liquid-tightness between the inner tube 55 and outer tube 58 needs to be secured at a position apart from the vibration nodes N in the longitudinal direction. In the present embodiment, by adopting the above-described configuration, liquid-tightness between the inner tube 55 and outer tube 58 can be secured by the inner seal portion 65, relay seal portion 75A, 75B and outer seal portion 71, even at a position apart from the vibration nodes N in the longitudinal direction, and the transmission of ultrasonic vibration to the inner seal portion 65, relay seal portion 75A, 75B and outer seal portion 71 can effectively be prevented.

(Modifications)

In the meantime, as illustrated in FIG. 9 as a first modification, the outer elastic member 63 may not be provided with the outer projection portion 72A, 72B. FIG. 9 illustrates a cross section which is perpendicular to the longitudinal axis C and passes through the inner seal portion (first seal portion) 65, relay seal portion (second seal portion) 75A, 75B and outer seal portion (third seal portion) 71. In the present modification, a projection end (outer end) of the inner projection portion 66A, 66b is put in close contact with the inner peripheral surface of the outer seal portion (third seal portion) 71. Accordingly, in this modification, the relay seal portion (second seal portion) 75A, which keeps the divided part (engaging part) D1 liquid-tight, is formed by only the inner projection portion 66A, and the relay seal portion (second seal portion) 75B, which keeps the divided part (engaging part) D2 liquid-tight, is formed by only the inner projection portion 66B.

Additionally, as illustrated in FIG. 10 as a second modification, the inner elastic member 62 may not be provided with the inner projection portion 66A, 66B. FIG. 10 illustrates a cross section which is perpendicular to the longitudinal axis C and passes through the inner seal portion (first seal portion) 65, relay seal portion (second seal portion) 75A, 75B and outer seal portion (third seal portion) 71. In the present modification, a projection end (inner end) of the outer projection portion 72A, 72b is put in close contact with the outer peripheral surface of the inner seal portion (first seal portion) 65. Accordingly, in this modification, the relay seal portion (second seal portion) 75A, which keeps the divided part (engaging part) D1 liquid-tight, is formed by only the outer projection portion 72A, and the relay seal portion (second seal portion) 75B, which keeps the divided part (engaging part) D2 liquid-tight, is formed by only the outer projection portion 72B.

Figure 11:
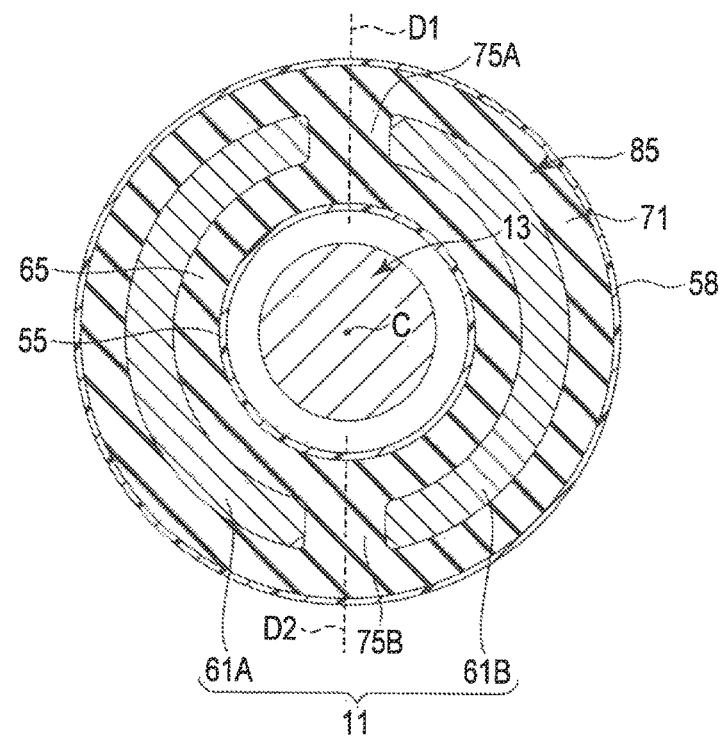
FIG. 11 is a cross-sectional view which schematically illustrates a cross section which is perpendicular to a longitudinal axis and passes through an inner seal portion, a relay seal portion and an outer seal portion according to a third modification.

Additionally, as illustrated in FIG. 11 as a third modification, the inner seal portion (first seal portion) 65, relay seal portion (second seal portion) 75A, 75B and outer seal portion (third seal portion) 71 may be formed of a single elastic member 85 as one piece. FIG. 11 illustrates a cross section which is perpendicular to the longitudinal axis C and passes through the inner seal portion (first seal portion) 65, relay seal portion (second seal portion) 75A, 75B and outer seal portion (third seal portion) 71. In the present modification, at the divided part D1, the relay seal portion 75A is continuous between the inner seal portion 65 and outer seal portion 71, and, at the divided part D2, the relay seal portion 75B is continuous between the inner seal portion 65 and outer seal portion 71.

Figure 12:
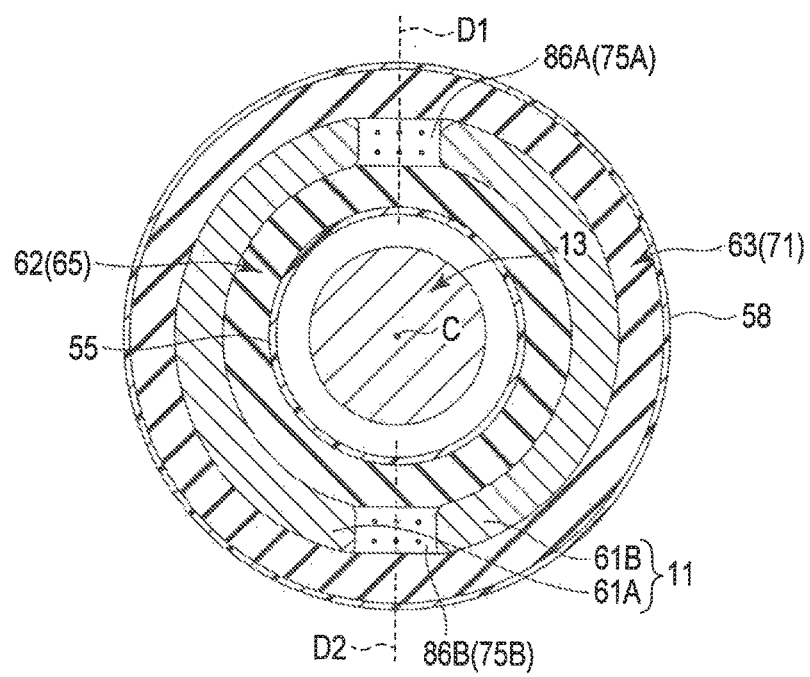
FIG. 12 is a cross-sectional view which schematically illustrates a cross section which is perpendicular to a longitudinal axis and passes through an inner seal portion, a relay seal portion and an outer seal portion according to a fourth modification.

Additionally, in a fourth modification illustrated in FIG. 12, the inner elastic member 62 is not provided with the inner projection portion 66A, 66B, and the outer elastic member 63 is not provided with the outer projection portion 72A, 72B. Accordingly, in the present modification, the entirety of the inner elastic member 62 is the inner seal portion (first seal portion) 65, and the entirety of the outer elastic member 63 is the outer seal portion (third seal portion) 71. FIG. 12 illustrates a cross section which is perpendicular to the longitudinal axis C and passes through the inner seal portion (first seal portion) 65, relay seal portion (second seal portion) 75A, 75B and outer seal portion (third seal portion) 71. In the present modification, a filler portion 86A is formed by filling an adhesive in the divided part D1, and the relay seal portion (second seal portion) 75A is formed by the filler portion 86A. Besides, a filler portion 86B is formed by filling an adhesive in the divided part D2, and the relay seal portion (second seal portion) 75B is formed by the filler portion 86B.

In the meantime, in a certain modification, in place of the inner elastic member 62, the inner seal portion (first seal portion) 65 may be formed by filling an adhesive between the inner tube 55 and sheath 11. Besides, in another modification, in place of the outer elastic member 63, the outer seal portion (third seal portion) 71 may be formed by filling an adhesive between the outer tube 58 and sheath 11.

Additionally, in a fifth modification illustrated in FIG. 13, an elastic portion 87A is inserted-formed as one piece with the sheath component 61A, and an elastic portion 87B is inserted-formed as one piece with the sheath component 61B. FIG. 13 illustrates a cross section which is perpendicular to the longitudinal axis C and passes through the inner seal portion (first seal portion) 65, relay seal portion (second seal portion) 75A, 75B and outer seal portion (third seal portion) 71. In addition, in FIG. 13, the probe 13, inner tube 55 and outer tube 58 are omitted. In the present modification, the inner elastic member 62 is not provided with the inner projection portion 66A, 66B, and the entirety of the inner elastic member 62 is the inner seal portion (first seal portion) 65. Further, in this modification, the outer elastic member 63 is not provided. In this modification, by forming the sheath 11 by assembling the sheath component 61A and sheath component 61B, the relay seal portion (second seal portion) 75A, 75B is formed by a part of the elastic portion 87A that is insert-formed in the sheath component 61A. Besides, by forming the sheath 11, the outer seal portion (third seal portion) 71 is formed by another part of the elastic portion 87A that is insert-formed in the sheath component 61A, and by the elastic portion 87B that is insert-formed in the sheath component 61B.

Figure 14:
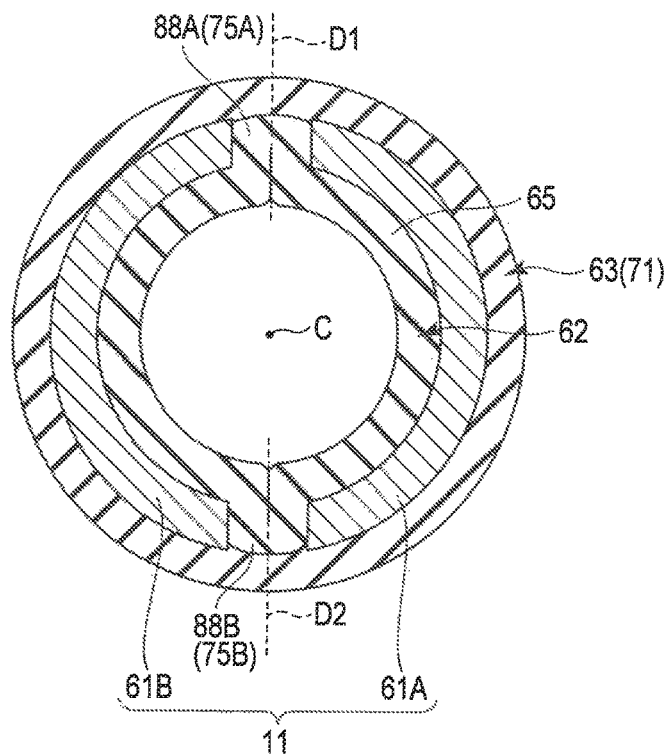
FIG. 14 is a cross-sectional view which schematically illustrates, in cross section perpendicular to a longitudinal axis, an inner seal portion, a relay seal portion, an outer seal portion and a sheath according to a sixth modification.

Additionally, in a sixth modification illustrated in FIG. 14, instead of not providing the inner elastic member 62 with the inner projection portion 66A, 66B, a radius R1 of the inner elastic member 62 is made greater than a radius R2 of the sheath 11, in the state in which the inner elastic member 62 is not clamped between the sheath component 61A and sheath component 61B. FIG. 14 illustrates a cross section which is perpendicular to the longitudinal axis C and passes through the inner seal portion (first seal portion) 65, relay seal portion (second seal portion) 75A, 75B and outer seal portion (third seal portion) 71. In addition, in FIG. 14, the probe 13, inner tube 55 and outer tube 58 are omitted. The radius R1 of the inner elastic member 62 is greater than the radius R2 of the sheath 11. Thus, in this modification, by clamping the inner elastic member 62 between the sheath component 61A and sheath component 61B, a turnup portion 88A is formed at the divided part D1 and a turnup portion 88B is formed at the divided part D2 by the inner elastic member 62. In the present modification, the inner seal portion (first seal portion) 65 is formed by that part of the inner elastic member 62, which excludes the turnup portions 88A and 88B. In addition, the relay seal portion (second seal portion) 75A is formed by the turnup portion 88A, and the relay seal portion (second seal portion) 75B is formed by the turnup portion 88B.

Figure 15:
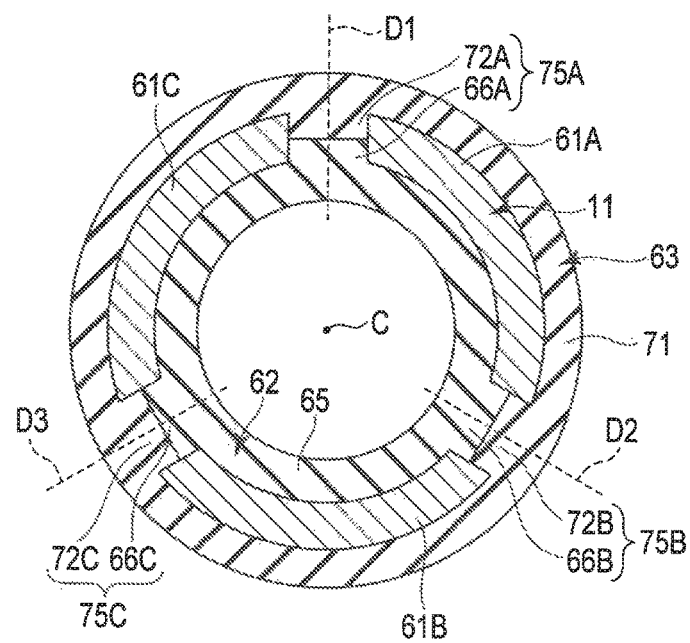
FIG. 15 is a cross-sectional view which schematically illustrates, in cross section perpendicular to a longitudinal axis, an inner seal portion, a relay seal portion, an outer seal portion and a sheath according to a seventh modification.

Additionally, in the first embodiment, the sheath 11 is divided into the two sheath components 61A and 61B, but the restriction to this is unnecessary. For example, as illustrated in FIG. 15 as a seventh modification, the sheath 11 may be divided into three sheath components 61A to 61C. FIG. 15 illustrates a cross section which is perpendicular to the longitudinal axis C and passes through the inner seal portion (first seal portion) 65, relay seal portions (second seal portions) 75A to 75C, and outer seal portion (third seal portion) 71. In addition, in FIG. 15, the probe 13, inner tube 55 and outer tube 58 are omitted. Also in this modification, in the sheath 11, each of the sheath components 61A to 61C is divided from the neighboring sheath components (corresponding two of 61A to 61C) at dividing planes (corresponding two of D1 to D3) which are parallel to the longitudinal axial direction.

In the present modification, too, the inner seal portion (first seal portion) 65, which keeps liquid-tightness between the inner tube 55 and sheath 11, is formed in the inner elastic member 62. In addition, the outer seal portion (third seal portion) 71, which keeps liquid-tightness between the sheath 11 and outer tube 58, is formed in the outer elastic member 63. In this modification, the relay seal portion (second seal portion) 75A, which keeps liquid-tight the divided part (engaging part) D1 between the sheath component (first sheath component) 61A and sheath component (third sheath component) 61C, is formed by the inner projection portion (first projection portion) 66A of the inner elastic member 62 and the outer projection portion (second projection portion) 72A of the outer elastic member 63. In addition, the relay seal portion (second seal portion) 75B, which keeps liquid-tight the divided part (engaging part) D2 between the sheath component (first sheath component) 61A and sheath component (second sheath component) 61B, is formed by the inner projection portion 66B of the inner elastic member 62 and the outer projection portion 72B of the outer elastic member 63. Besides, the relay seal portion (second seal portion) 75C, which keeps liquid-tight the divided part (engaging part) D3 between the sheath component (second sheath component) 61B and sheath component (third sheath component) 61C, is formed by the inner projection portion 66C of the inner elastic member 62 and the outer projection portion 72C of the outer elastic member 63. Accordingly, in this modification, too, even when liquid flowed in from the distal side to each of the divided parts D1 to D3, the liquid is prevented from entering to the proximal side from the corresponding relay seal portion (corresponding one of 75A to 75C) at each of the divided parts D1 to D3.

From the above-described seventh modification, it should suffice if the sheath 11 is formed of a plurality of sheath components (61A, 61B; 61A to 61C), and each of the sheath components (61A, 61B; 61A to 61C) is divided from the neighboring sheath component(s) (61A or 61B; corresponding two of 61A to 61C) at the dividing planes (D1 and D2; corresponding two of D1 to D3) which are parallel to the longitudinal axial direction.

Figure 16:
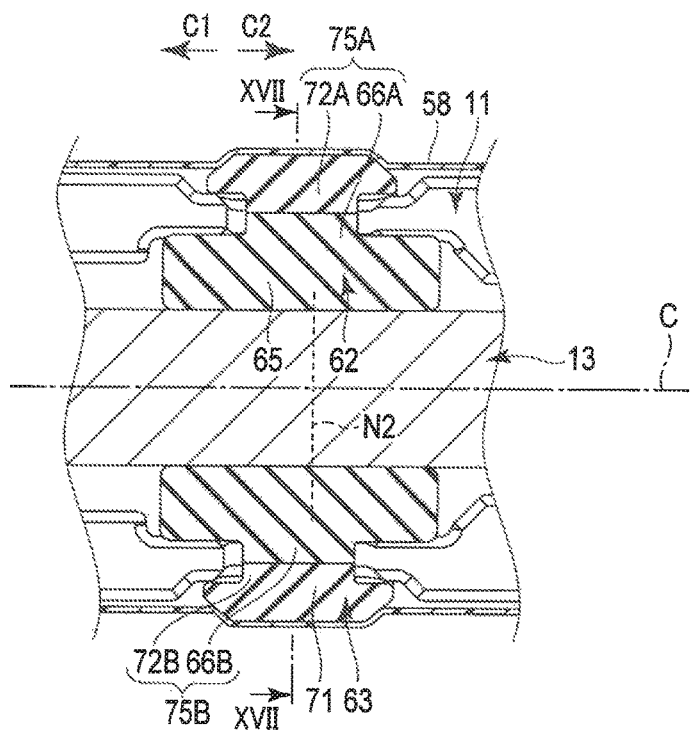
FIG. 16 is a cross-sectional view which schematically illustrates, in cross section perpendicular to a rotational axis of the jaw, the vicinity of an inner seal portion, a relay seal portion and an outer seal portion according to an eighth modification.
Figure 17:
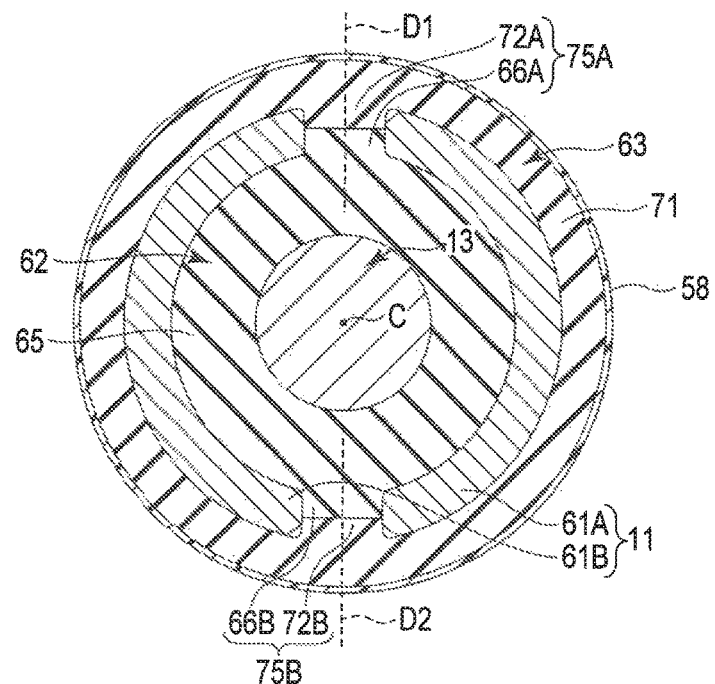
FIG. 17 is a cross-sectional view taken along line XVII-XVII in FIG. 16.

Additionally, in an eighth modification illustrated in FIG. 16 and FIG. 17, the inner tube 55 is not provided. FIG. 16 illustrates, in cross section perpendicular to the rotational axis P of the jaw 18, the vicinity of the inner seal portion (first seal portion) 65, relay seal portion (second seal portion) 75A, 75B and outer seal portion (third seal portion) 71. In addition, FIG. 17 is a cross-sectional view taken along line XVII-XVII in FIG. 16. Specifically, FIG. 17 illustrates a cross section which is perpendicular to the longitudinal axis C and passes through the inner seal portion (first seal portion) 65, relay seal portion (second seal portion) 75A, 75B, and outer seal portion (third seal portion) 71. In the present modification, since the inner tube 55 is not provided, the intervening portion 56, which keeps liquid-tightness between the probe 13 and inner tube 55, is not provided.

In the present modification, liquid-tightness between the probe 13 and sheath 11 is kept by the inner seal portion (first seal portion) 65 which is provided in the inner elastic member 62. Thus, the flow of liquid to the proximal side is prevented by the inner seal portion 65 between the probe 13 and sheath 11 in the radial direction. Accordingly, in this modification, too, the inner seal portion 65 prevents the flow of liquid toward the proximal side in the inside of the sheath 11.

Additionally, in this modification, too, liquid-tightness between the sheath 11 and outer tube 58 is kept by the outer seal portion (third seal portion) 71 of the outer elastic member 63. Besides, the relay seal portion (second seal portion) 75A, which keeps liquid-tight the divided part D1 of the sheath 11, is formed by the inner projection portion 66A of the inner elastic member 62 and the outer projection portion 72A of the outer elastic member 63, and the relay seal portion (second seal portion) 75B, which keeps liquid-tight the divided part D2 of the sheath 11, is formed by the inner projection portion 66B of the inner elastic member 62 and the outer projection portion 72B of the outer elastic member 63.

Additionally, in the present modification, the inner seal portion (first seal portion) 65, relay seal portion (second seal portion) 75A, 75B and outer seal portion (third seal portion) 71 are not spaced apart in the longitudinal axial direction. Thus, liquid-tightness is kept between the probe 13 and outer tube 58 by the inner seal portion 65, relay seal portion 75A, 75B and outer seal portion 71. Accordingly, the flow of liquid to the proximal side from the position, where the inner seal portion 65, relay seal portion 75A, 75B and outer seal portion 71 are disposed, is prevented between the probe 13 and outer tube 58 in the radial direction.

Accordingly, in this modification, too, when liquid has flowed in the inside of the sheath 11 from the opening at the distal end of the sheath 11, the flow of the liquid to the proximal side from the position, where the inner seal portion 65, relay seal portion 75A, 75B and outer seal portion 71 are disposed, is prevented. Thereby, the liquid, which has flowed in the inside of the sheath 11 from the distal end of the sheath 11, can effectively be prevented from flowing into the inside of the held unit 10.

Additionally, in this modification, in the state in which the vibrating body unit 20 including the probe 13 vibrates in the predetermined vibration state (at the predetermined resonance frequency), a vibration node N2, which is one of the vibration nodes N, is located at a position which is not spaced apart from the inner seal portion (first seal portion) 65, relay seal portion (second seal portion) 75A, 75B and outer seal portion (third seal portion) 71 in the longitudinal axial direction. Specifically, in the state in which the vibrating body unit 20 vibrates in the predetermined vibration state, the position of the vibration node N2 substantially agrees with the inner seal portion 65, relay seal portion 75A, 75B and outer seal portion 71 in the longitudinal axial direction. In addition, the sheath 11 is held by the inner seal portion (first seal portion) 65 in a state of non-contact with the probe 13. Thus, in the state in which the vibrating body unit 20 vibrates in the predetermined vibration state, no ultrasonic vibration is transmitted from the probe 13 to the inner seal portion (first seal portion) 65, relay seal portion (second seal portion) 75A, 75B and outer seal portion (third seal portion) 71. Accordingly, it is possible to effectively prevent the inner seal portion 65, relay seal portion 75A, 75B and outer seal portion 71 from being worn due to vibration.

In the meantime, from the standpoint of securing liquid-tightness between the probe 13 and outer tube 58, it is not always necessary that the vibration node N2 be located at the position which is not spaced apart from the inner seal portion 65, relay seal portion 75A, 75B and outer seal portion 71 in the longitudinal axial direction. Specifically, each of the vibration nodes N may be spaced apart from the inner seal portion 65, relay seal portion 75A, 75B and outer seal portion 71 in the longitudinal axial direction.

Additionally, in the above-described embodiment, etc., the movable handle 17 opens or closes in the direction crossing the longitudinal axis C. However, for example, the movable handle 17 may be configured to open or close substantially in parallel to the longitudinal axis C.

In the above-described embodiment, etc., a surgical treatment instrument (2) includes a probe (13) which has a proximal end and a distal end, and which extends in a longitudinal axial direction (C1, C2) that is parallel to a longitudinal axis (C); and a sheath (11) which includes a plurality of sheath components (61A, 61B; 61A to 61C) and extends in the longitudinal axial direction, and through which the probe (13) is inserted. In the sheath (11), each of the sheath components (61A, 61B; 61A to 61C) is divided from the neighboring sheath component(s) (61A or 61B; corresponding two of 61A to 61C) at dividing planes (D1 and D2; corresponding two of D1 to D3) along the longitudinal axial direction. A first seal portion (65) is provided between the sheath (11) and the probe (13) in a radial direction, and a flow of liquid to a proximal side (C2) is prevented by the first seal portion (65) in an inside of the sheath (11). In addition, a divided part between each of the sheath components and the neighboring sheath component is kept liquid-tight by a second seal portion (75A, 75B; 75A to 75C), and a flow of the liquid to the proximal side is prevented by the second seal portion at the divided part of each of the sheath components from the neighboring sheath component.

Reference Example

Figure 18:
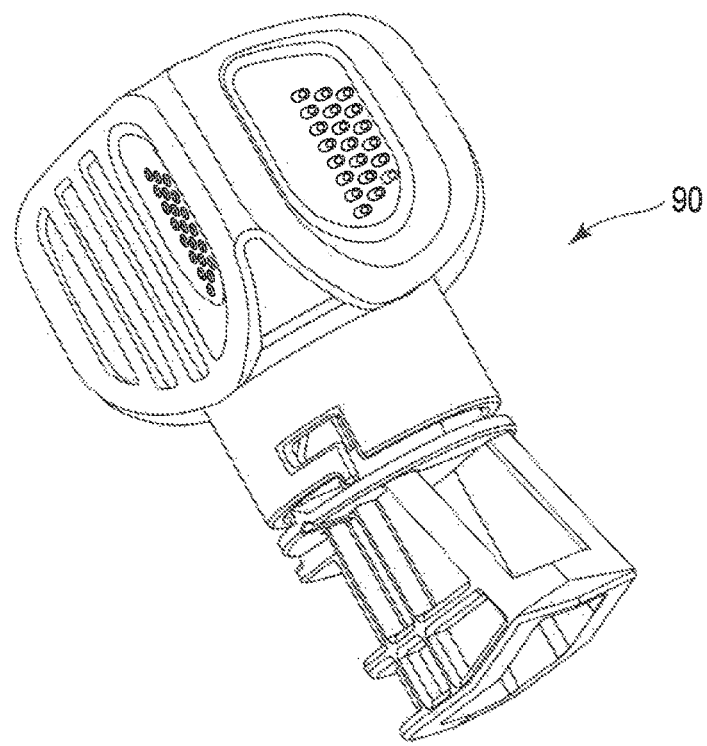
FIG. 18 is a perspective view illustrating a torque wrench according to a reference example.
Figure 19:
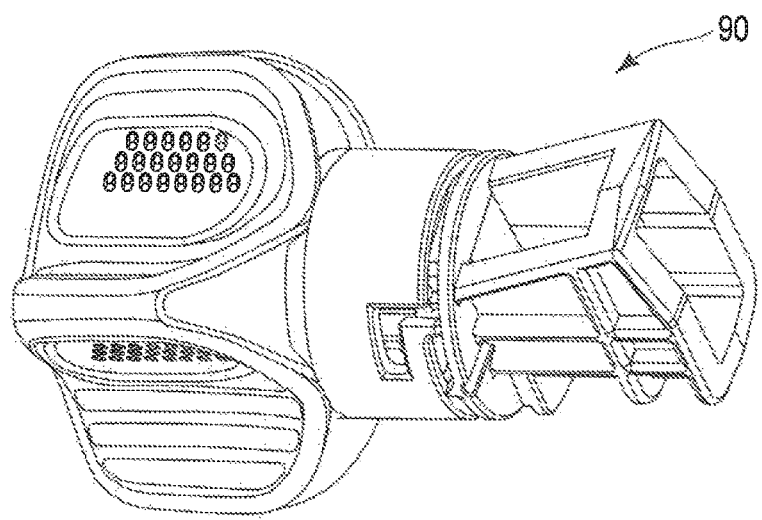
FIG. 19 is a perspective view illustrating the torque wrench according to the reference example, as viewed in a direction different from the direction in FIG. 18.
Figure 20:
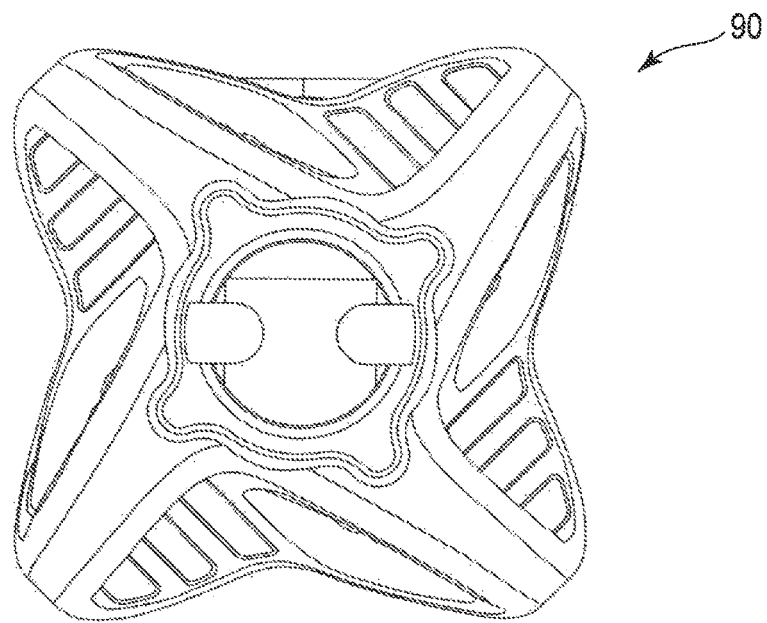
FIG. 20 is a front view illustrating the torque wrench according to the reference example.
Figure 21:
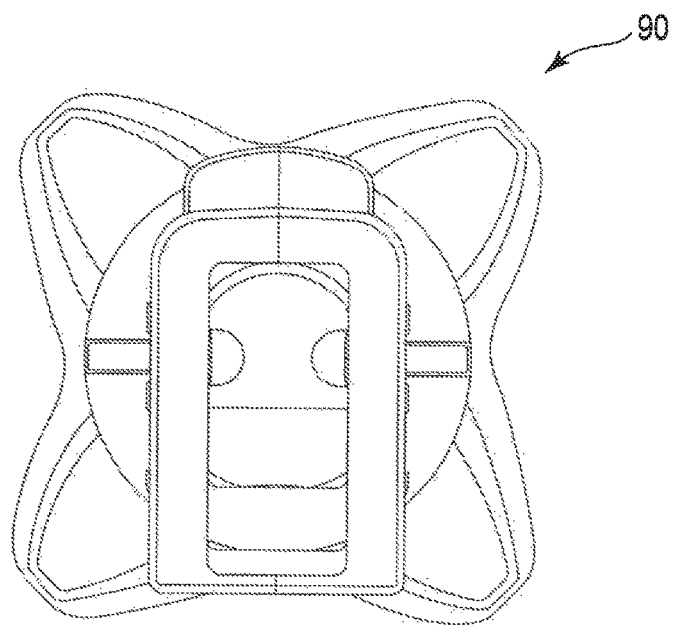
FIG. 21 is a rear view illustrating the torque wrench according to the reference example.
Figure 22:
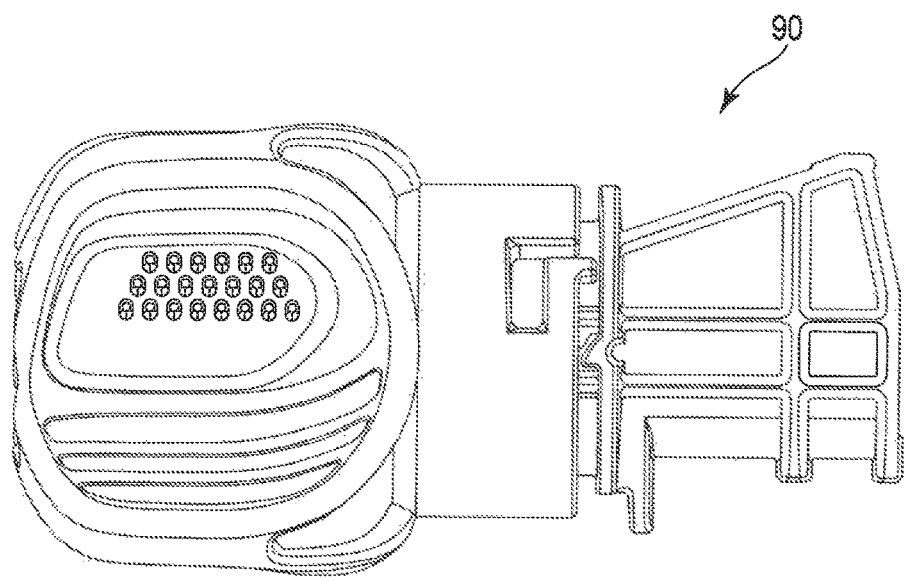
FIG. 22 is a right side view illustrating the torque wrench according to the reference example.
Figure 23:
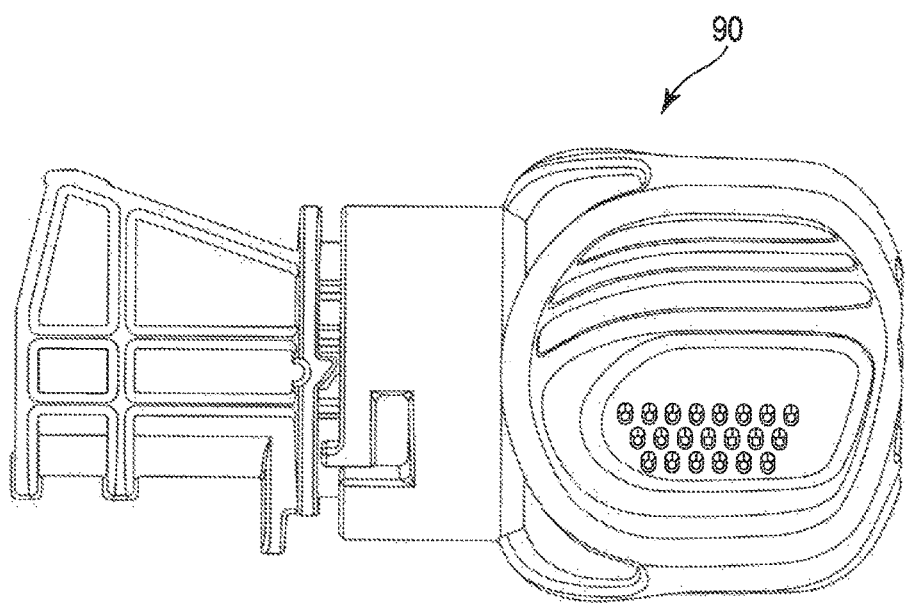
FIG. 23 is a left side view illustrating the torque wrench according to the reference example.
Figure 24:
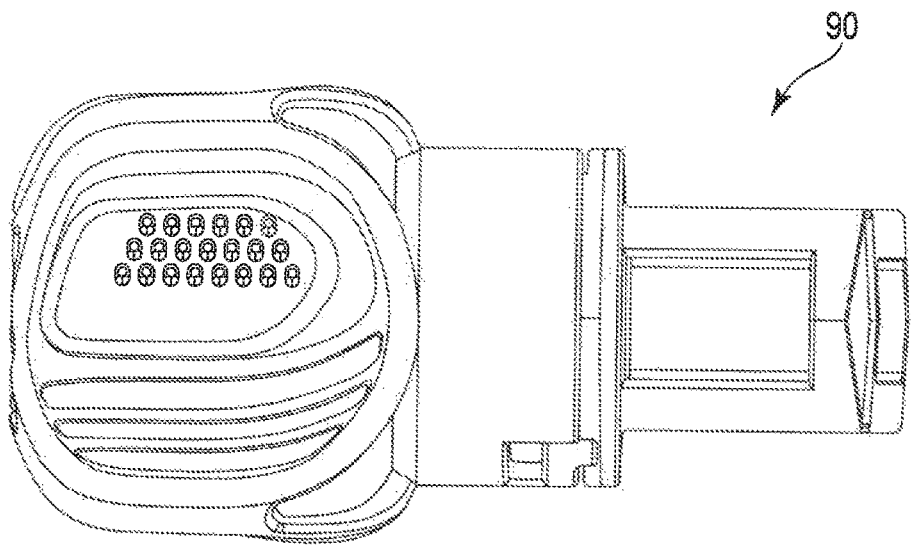
FIG. 24 is a plan view illustrating the torque wrench according to the reference example.
Figure 25:
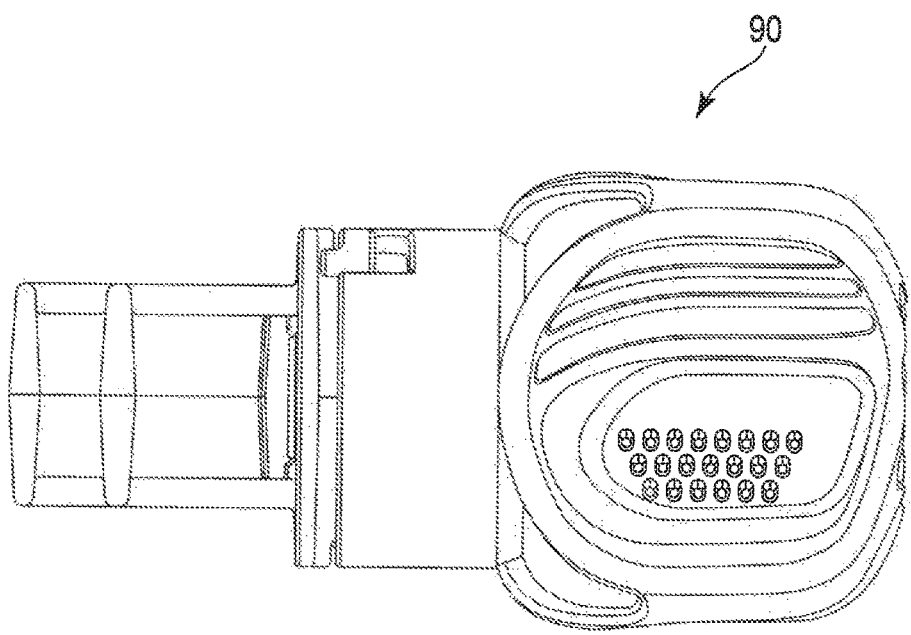
FIG. 25 is a bottom view illustrating the torque wrench according to the reference example.

Additionally, as a reference example, a torque wrench 90 illustrated in FIG. 18 to FIG. 25 is used in a work of attaching the transducer unit 3 to the surgical treatment instrument 2. FIG. 18 and FIG. 19 are perspective views of the torque wrench 90. In addition, FIG. 20 is a front view, FIG. 21 is a rear view, FIG. 22 is a right side view, FIG. 23 is a left side view, FIG. 24 is a plan view (top view), and FIG. 25 is a bottom view.

In the work of attaching the transducer unit 3 to the surgical treatment instrument 2, the torque wrench 90 is attached to the surgical treatment instrument 2 in the state in which the rear side thereof faces the proximal side. At this time, the sheath 11 is inserted through the torque wrench 90, and the torque wrench 90 is attached to the held unit 10 from the distal side. Then, the transducer unit 3 is inserted in the inside of the held unit 10 from the proximal side, and the surgical treatment instrument 2 is rotated relative to the transducer unit 3 about the longitudinal axis C by using the torque wrench 90. Thereby, the transducer unit 3 is attached to the surgical treatment instrument 2.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical treatment instrument comprising:
a probe having a proximal end and a distal end, and extending in a longitudinal axial direction;
a sheath including a plurality of sheath components having inner and outer surfaces and longitudinal edges that (1) abut along a dividing plane which extends along the longitudinal axial direction and (2) extend in the longitudinal axial direction, the sheath being configured to have such a cylindrical shape that the probe is insertable therethrough by the plurality of sheath components being abutted on each other at the dividing plane, and the sheath components having a recess portion which is recessed in a circumferential direction from the longitudinal edges at the dividing plane, and the sheath having an opening defined by the recess portion that extends between and through the inner and outer surfaces of the sheath components;
a first seal portion provided between the sheath and the probe in a radial direction at a position which is not spaced apart from the recess portion in the longitudinal axial direction, and configured to prevent a flow of liquid to a proximal side in an inside of the sheath; and
a second seal portion provided in the recess portion, and configured to prevent a flow of the liquid to the proximal side at the dividing plane of each of the sheath components from the neighboring sheath component.

2. The surgical treatment instrument of claim 1, wherein the plurality of sheath components include a first sheath component and a second sheath component which neighbors the first sheath component, and
the second seal portion projects from an outer peripheral surface of the first seal portion toward the dividing plane between the first sheath component and the second sheath component.

3. The surgical treatment instrument of claim 1, further comprising a third seal portion provided at a position which is not spaced apart from the first seal portion and the second seal portion in the longitudinal axial direction, the third seal portion covering an entire periphery of the sheath.

4. The surgical treatment instrument of claim 3, further comprising an outer tube which extends in the longitudinal axial direction, and through which the sheath is inserted,
wherein the third seal portion is configured to keep liquid-tightness between the sheath and the outer tube, and configured to prevent a flow of the liquid to the proximal side between the sheath and the outer tube.

5. The surgical treatment instrument of claim 3, wherein the plurality of sheath components include a first sheath component and a second sheath component which neighbors the first sheath component, and
the second seal portion projects from an inner peripheral surface of the third seal portion toward the dividing plane between the first sheath component and the second sheath component.

6. The surgical treatment instrument of claim 1, further comprising an inner tube which extends in the longitudinal axial direction and is provided between the sheath and the probe in the radial direction, and through which the probe is inserted,
wherein the first seal portion is configured to keep liquid-tightness between the inner tube and the sheath, and configured to prevent a flow of the liquid to the proximal side between the sheath and the inner tube.

7. The surgical treatment instrument of claim 6, further comprising an intervening portion provided between the probe and the inner tube in the radial direction, and configured to keep liquid-tightness between the probe and the inner tube, the intervening portion being configured to prevent a flow of the liquid to the proximal side between the probe and the inner tube.

8. The surgical treatment instrument of claim 7, wherein the intervening portion is provided apart from the first seal portion and the second seal portion in the longitudinal axial direction, and
the inner tube is held out of contact with the probe at a position other than the intervening portion in the longitudinal axial direction in a state in which a pushing force toward an inner peripheral side of the inner tube acts on the inner tube.

9. The surgical treatment instrument of claim 8, wherein the probe is capable of transmitting ultrasonic vibration, and is configured to vibrate in a predetermined vibration state by transmitting the ultrasonic vibration from the proximal side to the distal side, and
in a state in which the probe vibrates in the predetermined vibration state, one of vibration nodes of the ultrasonic vibration is located at a position which is not spaced apart from the intervening portion in the longitudinal axial direction, and the vibration nodes are spaced apart from the first seal portion and the second seal portion in the longitudinal axial direction.

10. The surgical treatment instrument of claim 1, wherein the first seal portion is configured to keep liquid-tightness between the probe and the sheath, and configured to prevent a flow of the liquid to the proximal side between the sheath and the probe.

11. The surgical treatment instrument of claim 10, wherein the probe is capable of transmitting ultrasonic vibration, and is configured to vibrate in a predetermined vibration state by transmitting the ultrasonic vibration from the proximal side to the distal side, and in a state in which the probe vibrates in the predetermined vibration state, one of vibration nodes of the ultrasonic vibration is located at a position which is not spaced apart from the first seal portion and the second seal portion in the longitudinal axial direction.

12. The surgical treatment instrument of claim 1, wherein the first seal portion and the second seal portion are formed as one piece.

13. The surgical treatment instrument of claim 1, wherein:
the plurality of sheath components comprises:
a first half pipe, and
a second half pipe configured to form the cylindrical shape with the first half pipe.

14. A surgical treatment instrument comprising:
a probe (1) having a proximal end and a distal end and (2) extending in a longitudinal axial direction;
a sheath housing the probe, the sheath including:
a pair of sheath components, each of the pair of sheath components includes inner and outer surfaces and first and second longitudinal edges that extend along the longitudinal axial direction, the pair of sheath components abutting each other at the first and second longitudinal edges, and
recesses in a circumferential direction between the abutting longitudinal edges;
an inner tube located inside the sheath that extends along the longitudinal axial direction;
an outer tube located outside the sheath that extends along the longitudinal axial direction;
a first seal portion between the inner tube and the sheath;
a third seal portion between the sheath and the outer tube; and
a second seal portion that extends through the recess between the first seal portion and the third seal portion.

15. The surgical treatment instrument of claim 14, wherein:
the first seal portion is a first seal;
the third seal portion is a second seal that is separate from the first seal; and
the second seal portion is integral with and extends from at least one of the first and second seals.

* * * * *